US005989215A

United States Patent [19]

Delmotte et al.

[11] Patent Number: 5,989,215

[45] Date of Patent: Nov. 23, 1999

[54] FIBRIN DELIVERY DEVICE AND METHOD FOR FORMING FIBRIN ON A SURFACE

[75] Inventors: Yves Delmotte, Tertre, Belgium; Arnold Bilstad, Deerfield, Ill.; David Amrani, Glendale, Wis.; Mark Kennedy, Crystal Lake; James DiOrio, Antioch, both of Ill.

[73] Assignee: Baxter International Inc., Deerfield, Ill.

[21] Appl. No.: 08/679,658

[22] Filed: Jul. 12, 1996

Related U.S. Application Data

[63] Continuation-in-part of application No. PCT/EP96/00160, Jan. 16, 1995.

[30] Foreign Application Priority Data

Jan. 16, 1995 [DE] Germany ........................... 195 01 067

[51] Int. Cl.[6] ........................ A61M 37/00

[52] U.S. Cl. ........................ 604/82; 604/191; 604/43

[58] Field of Search ........................ 604/82, 191, 43, 604/275, 283, 289; 222/134, 135, 136, 137

[56] References Cited

U.S. PATENT DOCUMENTS

| | | |
|---|---|---|
| 2,576,006 | 11/1951 | Ferry et al. . |
| 3,523,807 | 8/1970 | Gerendas . |
| 3,641,240 | 2/1972 | Hymes et al. . |
| 3,723,244 | 3/1973 | Breillatt, Jr. . |
| 4,116,898 | 9/1978 | Dudley et al. . |

(List continued on next page.)

FOREIGN PATENT DOCUMENTS

| | | |
|---|---|---|
| 0 068 149 A2 | 1/1983 | European Pat. Off. . |
| 0 085 166 A1 | 8/1983 | European Pat. Off. . |
| 0 103 290 A2 | 3/1984 | European Pat. Off. . |
| 0 166 263 A1 | 1/1986 | European Pat. Off. . |
| 0 187 894 A1 | 7/1986 | European Pat. Off. . |
| 0 213 563 B1 | 3/1987 | European Pat. Off. . |
| 0 262 890 A2 | 4/1988 | European Pat. Off. . |
| 0 369 764 A2 | 5/1990 | European Pat. Off. . |
| 0 372 969 A1 | 6/1990 | European Pat. Off. . |
| 0 479 615 A1 | 4/1992 | European Pat. Off. . |
| 0 485 210 A2 | 5/1992 | European Pat. Off. . |
| 0 485 210 A3 | 5/1992 | European Pat. Off. . |
| 0 534 178 A2 | 3/1993 | European Pat. Off. . |

(List continued on next page.)

OTHER PUBLICATIONS

Marchac, D., et al., The Use Of Sprayed Fibrin Glue For Face Lifts, European Journal of Plastic Surgery, 1987, vol. 10, pp. 139–143.

de Virgilio, Christian, M.D., et al., Fibrin Glue Inhibits Intra–abdominal Adhesion Formation, Archives of Surgery, Oct. 1990, vol. 125, pp. 1378–1382.

Redl, H., et al., In Vitro Properties Of Mixtures Of Fibrin Seal And Antibiotics, Biomaterials, Jan. 1983, vol. 4, pp. 29–32.

(List continued on next page.)

*Primary Examiner*—John G. Weiss
*Assistant Examiner*—David J. Cho
*Attorney, Agent, or Firm*—Wallenstein & Wagner, Ltd.

[57] ABSTRACT

This invention provides a medical device for delivering volumetric quantities of a first and a second biochemically reactive fluid comprising a first container having an opening, the first container being adapted to contain the first biochemically reactive fluid; a second container having a second fluid opening adjacent the first fluid opening, the second container being adapted to contain the second biochemically reactive fluid; a spray unit for separately atomizing the first and second biochemically reactive fluids into an aerosol with at least one energy source of a liquid energy, a mechanical energy, a vibration energy, and an electric energy; a fluid pressurizer for pressurizing the first and the second biochemically reactive fluids for delivery under pressure through the spray unit onto a surface; and wherein the first and second biochemically reactive fluids first mix on the surface.

7 Claims, 9 Drawing Sheets

U.S. PATENT DOCUMENTS

| | | | |
|---|---|---|---|
| 4,359,049 | 11/1982 | Redl et al. | 604/82 |
| 4,442,655 | 4/1984 | Stroetmann . | |
| 4,505,817 | 3/1985 | Blomback et al. . | |
| 4,505,822 | 3/1985 | Blombeck et al. . | |
| 4,537,767 | 8/1985 | Rothman et al. . | |
| 4,548,736 | 10/1985 | Müller et al. . | |
| 4,587,018 | 5/1986 | Blomback et al. . | |
| 4,600,574 | 7/1986 | Lindner et al. . | |
| 4,606,337 | 8/1986 | Zimmermann et al. . | |
| 4,631,055 | 12/1986 | Redl et al. . | |
| 4,640,778 | 2/1987 | Blombeck et al. . | |
| 4,675,361 | 6/1987 | Ward, Jr. . | |
| 4,683,142 | 7/1987 | Zimmermann et al. . | |
| 4,690,684 | 9/1987 | McGreevy et al. . | |
| 4,704,131 | 11/1987 | Noishiki et al. . | |
| 4,720,512 | 1/1988 | Hu et al. . | |
| 4,786,556 | 11/1988 | Hu et al. . | |
| 4,833,200 | 5/1989 | Noishiki et al. . | |
| 4,872,867 | 10/1989 | Joh . | |
| 4,874,368 | 10/1989 | Miller et al. . | |
| 4,882,148 | 11/1989 | Pinchuk . | |
| 4,909,251 | 3/1990 | Seelich . | |
| 4,911,926 | 3/1990 | Henry et al. . | |
| 4,932,942 | 6/1990 | Maslanka . | |
| 4,978,336 | 12/1990 | Capozzi et al. . | |
| 5,019,393 | 5/1991 | Ito et al. . | |
| 5,049,393 | 9/1991 | Noon et al. . | |
| 5,053,048 | 10/1991 | Pinchuk . | |
| 5,071,664 | 12/1991 | Viegas et al. . | |
| 5,080,893 | 1/1992 | Goldberg et al. . | |
| 5,112,615 | 5/1992 | Ito et al. . | |
| 5,116,315 | 5/1992 | Capozzi et al. | 604/82 |
| 5,126,140 | 6/1992 | Ito et al. . | |
| 5,140,016 | 8/1992 | Goldberg et al. . | |
| 5,153,003 | 10/1992 | Kurihara et al. . | |
| 5,156,613 | 10/1992 | Sawyer . | |
| 5,167,960 | 12/1992 | Ito et al. . | |
| 5,182,317 | 1/1993 | Winters et al. . | |
| 5,209,776 | 5/1993 | Bass et al. . | |
| 5,213,580 | 5/1993 | Slepian et al. . | |
| 5,223,420 | 6/1993 | Rabaud et al. . | |
| 5,244,799 | 9/1993 | Anderson . | |
| 5,260,420 | 11/1993 | Burnouf-Radosevich et al. . | |
| 5,278,200 | 1/1994 | Coury et al. . | |
| 5,364,622 | 11/1994 | Franz et al. . | |
| 5,368,563 | 11/1994 | Lonneman et al. | 604/82 |
| 5,376,376 | 12/1994 | Li . | |
| 5,376,692 | 12/1994 | Park et al. . | |
| 5,395,923 | 3/1995 | Bui-Khac et al. . | |
| 5,447,724 | 9/1995 | Helmus et al. . | |
| 5,455,040 | 10/1995 | Marchant . | |
| 5,464,396 | 11/1995 | Barta et al. | 604/191 |
| 5,486,357 | 1/1996 | Narayanan . | |
| 5,521,280 | 5/1996 | Reilly et al. . | |
| 5,525,348 | 6/1996 | Whitbourne et al. . | |
| 5,541,167 | 7/1996 | Hsu et al. . | |
| 5,541,305 | 7/1996 | Yokota et al. . | |
| 5,567,806 | 10/1996 | Abdul-Malak et al. . | |
| 5,578,073 | 11/1996 | Haimovich et al. . | |
| 5,580,923 | 12/1996 | Yeung et al. . | |
| 5,582,596 | 12/1996 | Fukunaga et al. | 604/191 |
| 5,665,067 | 9/1997 | Linder et al. | 604/82 |
| 5,697,903 | 12/1997 | Fischer | 604/82 |
| B1 4,225,580 | 10/1984 | Rothman et al. . | |

FOREIGN PATENT DOCUMENTS

| | | |
|---|---|---|
| 0 562 864 A1 | 9/1993 | European Pat. Off. . |
| 0 592 242 A1 | 4/1994 | European Pat. Off. . |
| 0 611 571 A1 | 8/1994 | European Pat. Off. . |
| 2 448 900 | 9/1980 | France . |
| 38 41 397 C2 | 11/1992 | Germany . |
| WO 89/02445 | 3/1989 | WIPO . |
| WO 91/01711 | 2/1991 | WIPO . |
| WO 91/19519 | 12/1991 | WIPO . |
| WO 92/15341 | 9/1992 | WIPO . |
| WO 92/22312 | 12/1992 | WIPO . |
| WO 93/19805 | 10/1993 | WIPO . |
| WO 93/21971 | 11/1993 | WIPO . |
| WO 94/02182 | 2/1994 | WIPO . |
| WO 94/22503 | 10/1994 | WIPO . |
| WO 96/17638 | 6/1996 | WIPO . |
| WO 96/22115 | 7/1996 | WIPO . |
| WO 96/39212 | 12/1996 | WIPO . |

OTHER PUBLICATIONS

Schier, F., et al., Dura Covered With Fibrin Glue Reduces Adhesions In Abdominal Wall Defects, European Journal of Pediatric Surgery 1, 1991, pp. 343–345.

Joyce, Douglas H., et al., Alteration In Pericardial Adhesion Formation Following Pretreatment With Fibrin Glue, Journal of Applied Biomaterials, 1991, vol. 2, pp. 269–271.

Tulandi, Togas, M.D., Effects Of Fibrin Sealant On Tubal Anastomosis And Adhesion Formation, Fertility and Sterility, Jul. 1991, vol. 56, No. 1, pp. 136–138.

Brands, W., et al., Die Anwendung Des Fibrinklebers zur Prophylaxe und Therapie intraabdomineller Adhasionen, Der Chirurg, 1990, vol. 61, pp. 22–26.

Giovanettoni, Lukas, The Tisseel Method, History, Background, Application, Techniques And Indications Of Fibrin Sealing In Modern Surgery, Immuno, Jan. 1985, pp. 1–70.

Bailey, Orville T., et al., Fibrin Films In Neurosurgery, With Special Reference To Their Use In The Repair Of Dural Defects And In The Prevention Of Meningocerebral Adhesions, Harvard Medical School, Feb. 17, 1944, Paper No. 27, pp. 597–600.

Ferry, John D., et al., Fibrin Clots, Fibrin Films, And Fibrinogen Plastics, Harvard Medical School, Feb. 17, 1994, Paper No. 22, pp. 566–572.

Sasaki, Takeru, et al., Stable Complex Of Fibrinogen And Fibrin, Science, May 20, 1966, vol. 152, pp. 1069–1071.

Copley, A. L., et al., The Binding Of Human Fibrinogen To Native And Fraction Fibrins And The Inhibition Of Polymerization Of A New Human Fibrin Monomer By Fibrinogen, Life Sciences, 1964, vol. 3, No. 11, pp. 1293–1305.

Chmielewski, Gary W., M.D., et al., Fibrin Gel Limits Intra–Abdominal Adhesion Formation, The American Surgeon, Sep. 1992, vol. 58, No. 9, pp. 590–593.

Sheppard, Barry B., M.D., et al., Inhibition Of Intra–Abdominal Adhesions: Fibrin Glue In A Long Term Model, The American Surgeon, Dec. 1993, vol. 59, No. 12, pp. 786–790.

Grey, Ernest G., M.D., Fibrin As A Haemostatic In Cerebral Surgery, Surgery, Gynecology And Obstetrics, pp. 452–454.

Hill–West, Jennifer, et al., Prevention Of Postoperative Adhesions In The Rat By In Situ Photopolymerization Of Bioresorbable Hydrogel Barriers, Obstetrics & Gynecology, Jan. 1994, vol. 83, No. 1, pp. 59–64.

Sawhney, Amarpreet S., et al., Optimization Of Photopolymerized Bioerodible Hydrogel Properties For Adhesion Prevention, Journal of Biomedical Materials Research, 1994, vol. 28, pp. 831, 833, 835, 837.

Sawhney, Amarpreet S., et al., Bioerodible Hydrogels Based On Photopolymerized Poly(ethylene glycol)–co–poly(α–hydroxy acid) Diacrylate Macromers, Macromolecules, 1993, vol. 26, No. 4, pp. 581–587.

Harvey, S. C., Dr., The Use Of Fibrin Paper And Forms In Surgery, Boston Medical and Surgical Journal, May 4, 1916, vol. CLXXIV, No. 1S, pp. 658–659.

Miyazaki, Shozo, et al., Use Of Fibrin As A Carrier For Drug Delivery: A Long–Acting Delivery System For Pilocarpine Into The Eye, Chem. Pharm. Bull., 1982, vol. 30, No. 9, pp. 3405–3407.

Oka, Hisashi, M.D., et al., Effect Of A Biologic Glue On The Leakage Rate Of Experimental Rectal Anastomoses, The American Journal of Surgery, May 1982, vol. 143, pp. 561–564.

Lindenberg, Svend, et al., Studies On Prevention Of Intra–Abdominal Adhesion Formation By Fibrin Sealant, Acta Chir Scand, 1985, 151, pp. 525–527.

Ferry, John D., et al., Preparation And Properties Of Serum And Plasma Proteins. IX. Human Fibrin In The Form Of An Elastic Film, Harvard Medical School, Feb. 1947, Paper No. 48, vol. 69, pp. 400–409.

Horn, Bela, et al., Treatment Of Stress Incontinence By A Fibrin Bioplast, British Journal of Obstetrics and Gynaecology, Jan. 1975, vol. 82, pp. 61–63.

Maddox, Yvonne T., et al., An Evaluation Of The Bionite Hydrophilic Contact Lens For Use In A Drug Delivery System, Annals of Ophthalmology, Sep. 1972, pp. 789–790, 793–794, 796, 798, 802.

Linsky, Cary B., et al., Adhesion Reduction In The Rabbit Uterine Horn Model Using An Absorbable Barrier TC–7, The Journal of Reproductive Medicine, Jan. 1987, vol. 32, No. 1, pp. 17–20.

Blombäck, Birger et al., Fibrin Gels And Their Possible Implication For Surface Hemorheology In Health And Disease, Annals New York Academy of Sciences, 1983, pp. 397–409.

Gauwerky, J. F. H., et al., The Effect Of Fibrin Glue And Peritoneal Grafts In The Prevention Of Intraperitoneal Adhesions, Archives of Gynecology and Obstetrics, 1990, vol. 247, pp. 161–166.

Thompson, J. N., et al., Reduced Human Peritoneal Plasminogen Activating Activity: Possible Mechanism Of Adhesion Formation, Br. J. Surg., Apr. 1989, vol. 76, No. 4, pp. 382–384.

Baker, J. W., et al., Mediastinal Fibrin Glue: Hemostatic Effect And Tissue Response In Calves, Ann. Thorac. Surg., 1989, vol. 47, pp. 450–452.

Connolly, John E., et al., The Prevention And Treatment Of Intestinal Adhesions, International Abstracts of Surgery, May 1960, vol. 110, No. 5, pp. 417–431.

Shimanuki, Takao, et al., Localized Prevention Of Postsurgical Adhesion Formation And Reformation With Oxidized Regenerated Cellulose, Journal of Biomedical Materials Research, 1987, vol. 21, pp. 173–185.

Sierra, David H., Fibrin Sealant Adhesive Systems: A Review Of Their Chemistry, Material Properties And Clinical Applications, Journal of Biomaterials Applications, Apr. 1993, vol. 7, pp. 309–352.

Feldman, Dale S., et al., Tissue Adhesives In Wound Healing, University of Alabama at Birmingham, May 1994, pp. 1–38.

Gabbay, Shlomo, The Need For Intensive Study Of Pericardial Substitution After Open Heart Surgery, Trans Am Soc Artif Intern Organs, 1990, vol. XXXVI, pp. 789–791.

Cronkite, Eugene P., et al., Use Of Thrombin And Fibrinogen In Skin Grafting, J. A. M. A., Apr. 1, 1944, vol. 124, No. 14, pp. 976–978.

Tarlov, I. M., M.D., et al., Plasma Clot Suture Of Nerves, Archives of Surgery, pp. 44–58.

Matsuda, T., et al., Photoinduced Prevention Of Tissue Adhesion, ASAIO Journal, 1992, pp. M154–M157.

Urry, D. W., et al., Properties And Prevention Of Adhesions Applications Of Bioelastic Materials, Mat. Res. Soc. Symp. Proc., 1993, vol. 292.

Fujita, S. M., et. al., Prevention Of Surgical Adhesions Using Aerosoled Biodegradable Polyesters, The 20th Annual Meeting of the Society for Biomaterials, Apr. 5–9, 1994.

Haney, A. F., M.D., et al., Expanded–Polytetrafluoroethylene But Not Oxidized Regenerated Cellulose Prevents Adhesion Formation And Reformation In A Mouse Uterine Horn Model Of Surgical Injury, Fertility and Sterility, Sep. 1993, vol. 60, No. 3, pp. 550–558.

The Surgical Membrane Study Group, Prophylaxis Of Pelvic Sidewall Adhesions With Gore–Tex Surgical Membrane: A Multicenter Clinical Investigation, Fertility and Sterility, Apr. 1992, vol. 57, No. 4, pp. 921–923.

Montz, F. J., M.D., et al., Effectiveness Of Two Barriers At Inhibiting Post–Radical Pelvic Surgery Adhesions, Gynecologic Oncology, 1993, vol. 48, pp. 247–251.

De Iaco, PierAndrea, M.D., et al., Fibrin Sealant In Laparoscopic Adhesion Prevention In The Rabbit Uterine Horn Model, Fertility and Sterility, Aug. 1994, vol. 62, No. 2, pp. 400–494.

SEQUENTIAL APPLICATION
SINGLE COATING

LEGEND

| IST LAYER

| 2ND LAYER t = APPLICATION TIME

SEQUENTIAL APPLICATION
DOUBLE COATING

LEGEND

| IST LAYER

| 2ND LAYER t = APPLICATION TIME

SIMULTANEOUS APPLICATION
SINGLE COATING

LEGEND

| IST LAYER

| 2ND LAYER t = APPLICATION TIME

SIMULTANEOUS APPLICATION
DOUBLE COATING

LEGEND

| IST LAYER

| 2ND LAYER t = APPLICATION TIME 4.8
52
73

2.3
2.3
2.3
2.3

11.5
RI
RI
12E
12E
12D
12D
4,7
RI
RI 22
15,5
33
26.5
R2
R5
R 3.3

RI
11
22
RI

FIBRIN DELIVERY DEVICE AND METHOD FOR FORMING FIBRIN ON A SURFACE

RELATED APPLICATIONS

This application is a continuation-in-part of PCT application number PCT/EP96/00160 filed Jan. 16, 1995 which claims priority from German patent application number 195 01 067.1 filed on Jan. 16, 1995.

TECHNICAL FIELD

This invention provides a medical device for simultaneously or sequentially delivering volumetric quantities of biochemically reactive fluids contained in separate containers and more particularly to a medical fluid delivery system for volumetrically delivering fibrinogen and thrombin to form fibrin on a surface.

BACKGROUND ART

One of the major problems in intra-abdominal surgery is the avoidance of post-operative adhesions. It is well-known that adhesions contribute to pain, immobility, retarded wound healing, and in particular to intestinal obstruction which even may be life-threatening. In the field of gynecological surgery, post-surgical adhesions involving female reproductive organs may result in infertility.

Each surgical procedure necessarily produces various forms of trauma where the abdominal cavity or other human cavity is opened for an inspection. Physiologically, the process of wound closure then starts when bleeding ceases upon formation of a hemostatic clot at the places where blood vessels are injured. The clot, at first comprising mainly platelets, is solidified by a fibrin network resulting from the activation of an enzyme cascade involving thrombin, factor XIII and calcium. Further steps on the way to the sealing of the wound are retraction of the hemostatic clot, invasion of various cell types including fibroblasts into the wound area and eventually the lysis of the fibrin network. Adhesions are thought to begin to form when the fibrin clot covering an injury comes into contact with an adjacent surface and the new connective tissue produced by the fibroblasts attach the two surfaces together.

The problems associated with adhesions often require a further operative procedure for removing/lysing the adhesions, called adhesiolysis, which, like the first operation, principally bears the risk of forming additional adhesions.

Accordingly, the prevention of adhesion formation is medically important. Among the different approaches for prevention of adhesion formation, one involves the use of materials as a physical or bio-mechanical barrier for the separation or isolation of traumatized tissues during the healing process. Both synthetic materials and natural materials have been used as a barrier to adhesion formation. Permanent, inert implants like Gore Tex® surgical membranes consisting of expanded polytetrafluoroethylene (PTFE) generally require a second operative procedure to remove them, while others such as surgical membranes of oxidized regenerated cellulose are biodegradable, but are thought to elicit an inflammatory response ultimately leading to adhesion formation (A. F. Haney and E. Doty, *Fertility and Sterility* 60, 550–558, 1993).

Fibrin sealants/glues are well-known in the art for use in hemostasis, tissue sealing and wound healing, and have been commercially available outside the United States for more than a decade. Fibrin glues have not been widely used for anti-adhesion purposes. Further, the practice of changing the concentrations of thrombin and fibrinogen to achieve a fibrin film having a desired pore size is also not widely practiced.

Fibrin glues mimic the last step of the coagulation cascade and are usually commercialized as kits comprising two main components. The first component is a solution comprising fibrinogen and factor XIII, while the second component is a thrombin calcium solution. After mixing of components, the fibrinogen is proteolytically cleaved by thrombin and thus converted into fibrin monomers. Factor XIII is also cleaved by thrombin into its activated form (FXIIIa). FXIIIa cross links the fibrin monomers to form a three-dimensional network commonly called “Fibrin Gel.”

Previous attempts to provide a thrombin and fibrinogen delivery device are known.

For example, one such device is disclosed in U.S. Pat. No. 4,978,336 Which discloses a dual syringe system. A device made by the assignee of the ’336 Patent, Hemaedics, Inc., is sold under the tradename DUOFLO. Each syringe distal end is attached to a common manifold 14 having a mixing chamber. Fibrinogen and thrombin solutions are mixed in the manifold 14 prior to application to a wound or other surface. The manifold has a discharge tip for delivering the mixed solution onto a surface. The shortcoming of this device is the propensity for the tip to clog. This occurs when solid fibrin is formed upon brief interruptions in the application process. Such interruptions are common in normal medical procedures. The likelihood of this occurring increases as the thrombin concentration increases especially thrombin concentrations of greater than 20 IU/ml. The ’336 Patent acknowledges the clogging problem and suggests solving the problem by replacing the clogged tip. (Col. 3, line 4–Col. 4, line 2). However, replacing clogged tips is impractical and unacceptable for minimally invasive surgeries where a cavity of an animal body is accessed through a small surgical opening.

Other techniques provide for applying beads of a solution of thrombin and calcium and a solution of fibrinogen and Factor XIII adjacent and in contact with one another on a surface. In this case, the thrombin and fibrinogen react primarily along interfacing surfaces while the remaining portions of the solutions are generally isolated from one another by the solid fibrin formed between them. Thus, there is inadequate mixing of the solutions to provide for a suitable fibrin film. Also, the unreacted fibrinogen is available to react with thrombin supplied by the body to promote the formation of adhesions.

U.S. Pat. No. 4,631,055 discloses another thrombin and fibrinogen delivery device having two syringes mounted in a holding frame 3 in parallel spaced relationship. A conical portion of a distal end each syringe is inserted into a connecting head. In one embodiment of the ’055 patent, mixing of fluids contained in each syringe occurs inside the connecting head and in another embodiment the mixing of the fluids occurs outside the mixing head. The connecting head also includes a channel to supply medicinal gas under pressure. The medicinal gas contacts the fluids at a mouth of the connecting head and conveys the fluids contained in the syringes to a surface.

Product literature commenting on a dual syringe device for delivering fibrinogen and thrombin and sold by the Assignee of the ’055 patent, reports that the device operates at gas pressures of about 30–65 psi. The momentum of the pressurized gas, especially when conveying entrained fluids, could possibly cause damage to tissue being treated by this device.

Finally, a device sold by Johnson & Johnson provided for applying a bovine thrombin and calcium chloride solution to a wound. In addition to possible issues raised by the use of bovine proteins, this procedure does not provide satisfactory hemostasis function in high blood flow situations. The thrombin is believed to be washed from the wound site by the flow of blood.

This invention overcomes these and other shortcomings in the prior art devices.

DISCLOSURE OF INVENTION

This invention provides a medical device for delivering volumetric quantities of a first and a second biochemically reactive fluid. The device comprises a first container having an opening, the first container is adapted to contain the first biochemically reactive fluid. A second container has a second fluid opening adjacent the first fluid opening; the second container is adapted to contain the second biochemically reactive fluid. A spray unit is in fluid communication with the first container and the second container, the spray unit being capable of separately atomizing the first and second biochemically reactive fluids into an aerosol with at least one energy source of a liquid energy, a mechanical energy, a vibration energy, and an electric energy. A fluid pressurizer is associated with the first and second containers for pressurizing the first and the second biochemically reactive fluids for delivery under pressure through the spray unit onto a surface. Wherein the first and second biochemically reactive fluids first mix on the surface. This device does not use any pressurized gas.

This invention also provides a method for delivering fibrin to a surface. The method comprises the steps of: (1) providing a liquid solution of fibrinogen; (2) providing a liquid solution of thrombin; (3) providing a spray unit in fluid communication with the fibrinogen and thrombin solutions, the spray unit being capable of separately atomizing the fibrinogen and the thrombin into an aerosol with at least one energy source of a liquid energy, a mechanical energy, a vibration energy, and an electric energy; (4) spraying the fibrinogen solution onto the surface with the spray unit; (5) spraying the thrombin solution separately from the fibrinogen onto the surface; and (6) mixing for the first time the fibrinogen with the thrombin on the surface to make fibrin.

This invention also provides a method for delivering fibrin to a surface within a cavity of a body of an animal to prevent the formation of adhesions. The method comprising the steps of: (1) providing a liquid solution of fibrinogen; (2) providing a liquid solution of thrombin; (3) providing a spray unit in fluid communication with the fibrinogen and thrombin solutions, the spray unit being capable of separately atomizing the fibrinogen and the thrombin fluids into an aerosol with at least one energy source of a liquid energy, a mechanical energy, a vibration energy, and an electric energy; (4) spraying the fibrinogen solution onto the surface with the spray unit; (5) spraying the thrombin solution separately from the fibrinogen solution onto the surface with the spray unit; and (6) mixing for the first time the fibrinogen with the thrombin on the surface to make a fibrin film capable of preventing the formation of adhesions proximate the fibrin film.

Preferably the medical devices of this invention operate at pressures that are generated by a hand-held device. This allows the present device to provide a cost effective and less complicated alternative to those medical devices that rely on pressurized gases as a means for atomizing fluids and conveying them to a surface to be treated.

It is contemplated that versions of the medical device shall be used in open-type surgeries such as laparotomic surgeries, topically and in minimally invasive surgeries such as laparoscopic surgeries. In open-type surgeries and minimally invasive surgeries, the present device may be used for hemostasis, tissue healing and antiadhesion purposes. In topical applications, the device may be used for treating burn patients during skin grafting procedures and to act as an antimicrobial agent.

The medical device is capable of simultaneously or sequentially delivering biochemically reactive fluids to a surface where they mix for the first time. In the sequential application, it is possible to repeat the procedure to incrementally form a fibrin film.

BEST MODE FOR CARRYING OUT THE INVENTION

Figure 1:
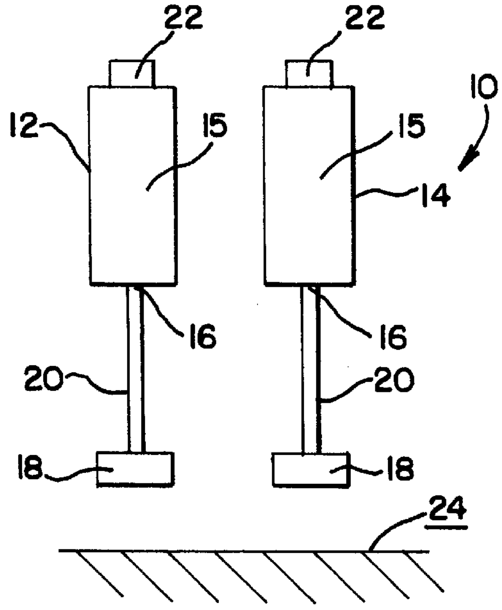
FIG. 1 is a schematic view of the device of this invention.

While the invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

This invention provides a method and apparatus for delivering two biochemically reactive liquids, preferably fibrinogen and thrombin, to form fibrin. These biochemically reactive fluids may be delivered topically, in open-type surgeries such as laparotomic surgeries and in minimally invasive surgical techniques such as, for example, laparoscopically. While it is well known to use fibrin for hemostasis purposes, it has been found that fibrin can be used to prevent the formation of adhesions in cavities of the human body. It is possible to manipulate the concentrations of fibrinogen and thrombin, especially thrombin, to effect a change in the characteristics of the resultant fibrin film. One such characteristic is the pore size of the film. By manipulating the concentrations of these fluids one can tailor the fibrin film that is best suited for its intended end use.

I. Fibrin Film

In a further aspect of the present invention, a combined use of a first fibrin glue acting as a hemostatic agent and of a second fibrin glue acting as a bio-mechanical barrier for the preparation of a medicament for the treatment of internal traumatic lesions is provided.

For the sake of convenience, the term "fibrin film" is used in the following to refer to a self-supporting sheet-like material of cross-linked fibrin. For the purposes of the invention, the fibrin film is composed of the same constituents as the fibrin glues on the market, i.e., mainly fibrinogen, thrombin, factor XIII and calcium.

Particularly advantageous is that the fibrin film does not considerably slip or move upon placement so that no fastening, like sutures, are required in the course of surgery. Due to its inherent mechanical properties, the fibrin film allows a tight cover over the traumatized tissue. Moreover, the fibrin film in terms of its composition and general structure is similar to the natural products formed upon injury in the human or animal body and, thus, they fulfill prime requirements an ideal surgical membrane would have, such as superior biocompatibility, biodegradability and bioresorbability. As a result and by marked contrast to barriers of inert materials like expanded PTFE, a bio-mechanical barrier made of fibrin disappears "by itself" after exerting its function so that no second surgical procedure for removal is required; in the animal model (rat) described below this usually occurs within ten days after the application of the fibrin film. Furthermore, it is appreciated that the fibrin film does not provoke any major side effects to the body.

In accordance with preferred embodiments of the invention, a self-supporting sheet-like material of cross-linked fibrin is provided, wherein said material has a regular pore size. The fibrin film of the invention has a dense, regular and homogenous structure within its entire volume as shown by Scanning Electron Microscopy (SEM). The pore size of the fibrin film is "regular" in the sense of varying only in a range of a few micrometers. It has been found that such a fibrin film is particularly effective in preventing adhesion formation.

On the other hand, according to experiments by the inventors, fibrin films having a more open or even irregular or non-homogenous structure including larger holes are not effective in this respect. Without being bound to a theory, this may be explained as follows. Such foam-, sponge- or fleece-like structures may allow the retention of blood set free during surgery and may further allow the ingrowth of fibroblasts, thus promoting endogenous fibrin formation accompanied by adhesion formation. Accordingly, such fibrin films, in particular in their dry state, may be useful in hemostasis to soak up the exudate of the injury. However, in anti-adhesion therapy, non-hemostatic fibrin films with non-adhesive properties are generally desired.

The fibrin film of the invention is insoluble in water and in the wet form may contain up to 92% by weight of water. Irrespective of being in hydrated (wet) or rehydrated state (e.g. after a previous drying step for storing), this fibrin film has a high mechanical strength, is by itself self-supporting and is yet soft. Thus, the fibrin film of the invention is easy to handle allows cutting, rolling and also suturing, if required. The self-supporting property of the fibrin film is reinforced by drying. The dry form of the fibrin film may be commercialized as part of a kit and is then to be rehydrated before use in surgery with appropriate solutions of e.g. water, calcium chloride, but also buffered solutions containing drugs.

Preferably, for the purposes of the present invention in certain embodiments, the pore size of the barrier material is below about 20 μm, more preferably below 5 μm, and most preferably below about 1 μm, to prevent fibroblasts from intruding or penetrating. As noted above, in the course of normal wound closure, fibroblasts migrate into the fibrin clot network and the developing granulation tissue, where they produce i.e., collagen and thus contribute to the ultimate formation of a scar tissue. In order to avoid that the substances produced by the fibroblasts contribute to glue, an injured surface and an adjacent surface or two injured surfaces together, the inventors propose to isolate or separate the injured surface(s) by using fibrin barrier material having a pore size, preferably a "regular" pore size in the sense of the present invention, of below 20 μm, preferably below 5 μm, preferably of below 4 μm, preferably of below 3 μm, preferably of below 2 μm and most preferably of below 1 μm or any combination of ranges between these sizes inclusive of the endpoints. In fact, experiments by the inventors described below demonstrate that by using such barriers the formation of adhesions can be prevented completely.

Usually, fibrin film in accordance with the invention is made of a single layer which, for the purpose of preventing adhesion formation, has a closed structure, but may also have an open structure for other applications. Moreover, the inventors propose a fibrin film comprising two or more layers. At least one layer, either as an outer layer or an intermediate layer, should have a closed structure ensuring the rigidity and/or the barrier function of the multi-layered fibrin film, whereas other layers having a open structure may work as a drug delivery system.

In preferred embodiments, the thickness of the fibrin barrier material is at least 20 μm when the barrier is in the wet state. Preferably the thickness is about 20–2000 μm, and most preferably up to 5000 μm, although it is believed that even material with a thickness of less than 20 μm may be suitable for the purposes of the invention.

It is well known that thrombin acts as a protease which will cleave fibrino peptide A and B from the fibrinogen molecule and convert it into fibrin. It is desirable that all of the fibrinogen be converted into fibrin, as residual amounts of fibrinogen may lead to adhesion formation upon reacting with thrombin provided by the body. The rate of the conversion of fibrinogen into fibrin increases as the concentration of thrombin increases, provided that there is a sufficient quantity of fibrinogen present. Preferably, thrombin is added at a ratio of 7 parts by weight for every 1 part by weight of fibrinogen, and more preferably within the range of 6 to 1 a more preferably within the range of 4 to 1 and most preferably 1 to 1. The rate of the conversion determines the pore size of the resultant fibrin film. The faster the conversion to fibrin the smaller the pore size of the resulting fibrin film. Using a thrombin solution having a concentration of about 3 IU/ml, approximately that found in the human body, produces a fibrin film with a relatively large pore size. The large pore size fibrin film is suitable for hemostasis and wound healing. Accordingly, in still further embodiments of the present invention, the fibrin film further comprises less than 5% by weight of fibrinogen, preferably less than 4% by weight of fibrinogen, preferably less than 3% by weight of fibrinogen, preferably less than 2% by weight of fibrinogen, and most preferably less than 1% by weight of fibrinogen, in terms of the total dry weight of the fibrinogen plus fibrin each time.

Generally speaking, the lower the amount of residual fibrinogen, the better the non-adhesive properties of the fibrin film, since fibrinogen in vivo may promote fibrin formation and thus adhesion formation. For the purpose of determining the fibrin and the fibrinogen content of the fibrin film, the methods of SDS-Page (SDS-Gelelectrophoresis) may be used.

It is preferred in certain embodiments that the fibrin film further comprises one or more disinfectants, preferably methylene blue, and/or one or more drugs selected from antibiotics, fibrinolytic agents and biological response modifiers, in particular cytokines and wound repair promoters, preferably in an amount up to 1% by weight in terms of the total dry weight of fibrin plus fibrinogen. Examples of fibrinolytic agents include t-PA, $\mu$-PA, streptokinase, staphylokinase, plasminogen and the like. These compounds promote fibrinolysis and thus can be used for controlling the rate of the degradation of the fibrin film in vivo. The term "biological response modifiers" is meant to refer to substances which are involved in modifying a biological response, such as wound repair, in a manner which enhances the desired therapeutic effect. Examples include cytokines, growth factors and the like. Due to its intrinsic mechanical properties, the fibrin film of the invention does not require any additional cross-linking agent which may exert any toxical effects to the human or animal body.

II. Biochemically Reactive Solutions

The components of the fibrinogen and thrombin can be prepared from plasma by conventional precipitation and purification steps. When the patient to be treated is a human being, human plasma will be preferred. The source of the plasma may be either pooled donor blood and single donor blood obtainable from blood centers, respectively. Care should be taken that state of the art controls are performed to detect viral contamination. During the process of manufacturing, the products may be sterilized by standard techniques as well. In order to avoid any risk of contamination, the components could be prepared from pre-operative autologous blood donation. It will be understood that the components of the first or the second solution or their functional analogues may also be prepared by using the methods of molecular genetics.

Conveniently, in the light of the present disclosure, commercially available two-component fibrin glue kits may be used for the preparation of the fibrin film of the present invention. The required constituents are usually contained in the kits in the form of lyophilized concentrates and have to be reconstituted as per the technical data sheet provided with the respective kit. The desired thrombin concentration is prepared by diluting an aliquot of the reconstituted thrombin solution with sterile calcium chloride solution, preferably 20 mM or 40 mM calcium chloride.

The inventors propose that the fibrin film of the invention may also be obtained from one vial containing all the required components, where the catalytic agents for the fibrinogen-fibrin conversion and the cross-linking of soluble fibrin, respectively, are inactivated and the polymerization is only started by induction through a change in pH, ionic strength, light and the like after the content of said vial had been applied to the solid support. By way of example, photo-sensitive inhibitors of thrombin and thrombin-like molecules could be used for this purpose. The fibrin film of the invention may also be prepared in accordance with Copley and Luchini, (*Life Sciences* 3, 1293–1305, 1964) and Sasaki et al. (*Science* 152, 1069–1071, 1966) by starting from soluble fibrinogen-fibrin monomer complexes precipitated in the cold, redissolved at high temperature and which are then cross-linked with F XIII and calcium.

In accordance with the invention, the first solution preferably contains fibrinogen and factor XIII (10–40 IU/ml). The concentration of fibrinogen is expressed as the total protein concentration (preferably from about 15–140 mg/l and more preferably 30–110 mg/ml) and the percentage of clottable protein comprised therein. It is also preferred that the fibrinogen solution have a viscosity that allows the solution to be sprayed and preferably sprayed using pressures generated using a hand-operated syringe. The fibrinogen solution should have a viscosity of less than 20 centipoise, more preferably less than 10 centipoise, and most preferably from 1–5 centipoise or any combination or subcombination of ranges therein.

The inventors prefer the percentage of clottable protein to be at least 80% and preferably equal to or greater than 90%. Of course, those of skill in the art will recognize that a variety of other constituents may be included in the first solution, for example albumin, plasminogen and tensides. The thrombin solution preferably comprises 3–10,000 IU/ml, even more preferably 200–500 IU/ml, and most preferably 400–500 IU/ml or any combination or subcombination of ranges therein (depending on the desired biophysical parameters of the material to be obtained) and calcium in a concentration of up to 45 mM. For simplification, the thrombin concentration normally given in IU/ml, will in the following frequently be indicated in IU, in particular in the Tables.

III. Delivery Device

FIG. 1 shows a schematic representation of a device 10 having a first container 12 and a second container 14. Each of the containers have a fluid channel 15 and a fluid opening 16. The opening 16 of each of the first and second containers 12 and 14 are associated with a spray unit 18. The spray unit 18 may be directly attached to the first and second containers 12 and 14 or be connected by other means such as a flexible medical tubing 20. A pressurizer 22 is associated with each of the first and second containers 12 and 14 for pressurizing fluids that will be contained therein for delivery to a surface 24. It is also possible to have a single pressurizer for both containers.

Figure 2:
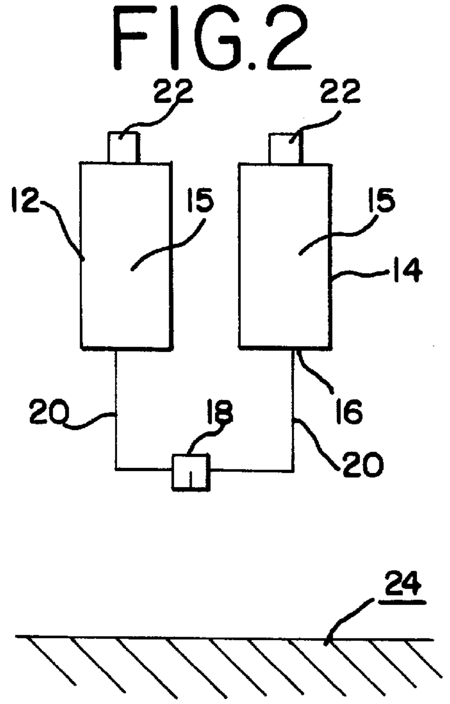
FIG. 2 is another embodiment of the device of this invention.
Figure 3:
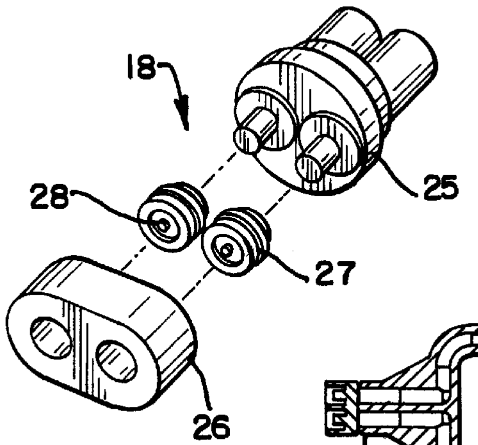
FIG. 3 is an assembly view in perspective of a spray unit.

FIG. 2 shows a delivery device having a single spray unit 18. FIG. 3 shows that the spray unit 18 is an assembly of several parts typically having an input piece 25, and an output piece 26 together sandwiching two mechanical break-up units (MBU) 27. Preferably the pieces 25 and 26 snap fit together for ease of assembly.

The MBU is what is known in the art as a jet swirl atomizer. The MBU's 27 have an inner surface having three converging tangential channels that define a fluid path that rotates in a clockwise direction as viewed from an inside surface of the MBU looking out. The channels direct the incoming fluid to a spin chamber to generate angular momentum in the fluid. The spinning fluid exits the MBU through a port 28 to form an aerosol.

It may be desirable to have one MBU having channels that follow a clockwise path and another adjacent MBU that has channels that travel counterclockwise. It is also possible that the MBU's 27 have from 2–4 channels per spray unit or more.

Several presently preferred MBUs are available from Seaquist Dispensing of Cary, Ill. under the product designations CS-5512, CS-5501, and CS-5503.

The device shown in FIG. 1 would have a single MBU per spray unit 18. The device shown in FIG. 2 would have the spray unit shown in FIG. 3 having two MBUs 27 per spray unit 18. Of course it is possible to incorporate more than two MBUs per spray unit 18.

Generally, it is possible to use several different energy types to form an aerosol from the biochemically reactive fluids. The preferred energy types are those selected from the group consisting of liquid energy, mechanical energy, vibration energy, and electric energy. This group excludes gas energy which is employed in U.S. Pat. No. 4,631,055 as the mechanisms necessary to generate the gas energy may be expensive and because the momentum of the gas energy stream that atomizes the fluids may be incompatible with and cause damage to certain delicate human tissues. Mechanisms capable of generating these energies and separately atomizing fluids may be referred to in the claims as a means for separately atomizing first and second fluid streams or the like.

Atomizers that use liquid energy are the preferred devices for generating an aerosol spray and include swirl atomizers and most preferably jet-swirl atomizers such as the MBUs 27 described above. An example of an atomizer employing mechanical energy includes rotary atomizers such as impellers or pumps. An example of devices employing vibration energy include acoustic and ultrasonic devices. An example of devices employing electric energy to create an aerosol spray include electrostatic devices. These are all well recognized energy sources for atomizing liquids as set forth in (L. Bayvel and Z. Orzechowski, *Liquid Atomization, pg.* 2).

These atomizing devices could also include a piezoelectric crystal that meters out small droplets of fluid based upon a cycle time of the piezoelectric crystal.

Preferably, the spray unit 18 has a diameter of 10 mm or less so that it may be passed through standard trocar devices which typically have diameters of from about 10 mm–12 mm and preferably 5 mm. Trocars are used to access internal cavities of an animal body during minimally invasive surgeries. The input device 25 shown in FIG. 3 has an external diameter of less than about 10 mm–12 mm.

It is also important that there be proper spacing between the two MBUs 27 to achieve mixing of the two biochemically reactive fluids on the surface 24. It is also important that the MBUs 27 have sufficient spacing to prevent mixing at the discharge port 28 of each MBU. Such mixing would cause fibrin to form at the exit port 28 thereby clogging the device 10. This invention further contemplates having a barrier wall (not shown) separating each MBU to prevent such mixing.

Figure 4:
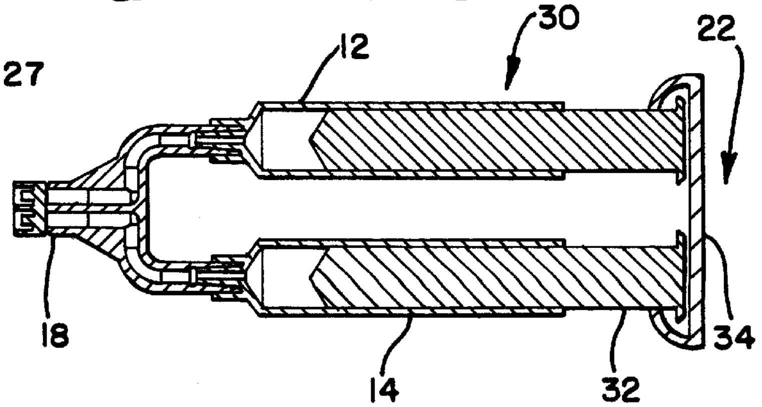
FIG. 4 is a perspective view of the device of this invention for open-type surgeries such as laparotomic uses.

As shown in FIG. 4, the containers 12 and 14 are preferably syringes and are attached together or are integral with one another to define a single unit 30. The syringes should be of a size commonly available and have volumes from about 1–20 cc and most preferably 10 cc. It is also preferable that the containers 12 and 14 have equal volumes.

The pressurizer 22 in this embodiment is a dual plunger having two horizontally spaced plungers 32 mechanically coupled at one end by a crossbar 34. FIG. 4 could also be modified such that distal ends of the containers 12 and 14 are dimensioned to fit directly into rear inlet ports 35 on the input device 25 (FIG. 3).

It should be understood that in place of the syringes, this invention contemplates using pipettes or other devices that are capable of dispensing accurate and determined volumes of liquid. One presently preferred pipette is a repeatable pipette sold by Eppendorf. The pressurizer could also be other devices capable of generating fluid pressure within a container such as a pump. The invention also contemplates using more than two containers to deliver additional fluids to the surface 24.

IV. Delivery Device for Minimally Invasive Surgery

Figure 5:
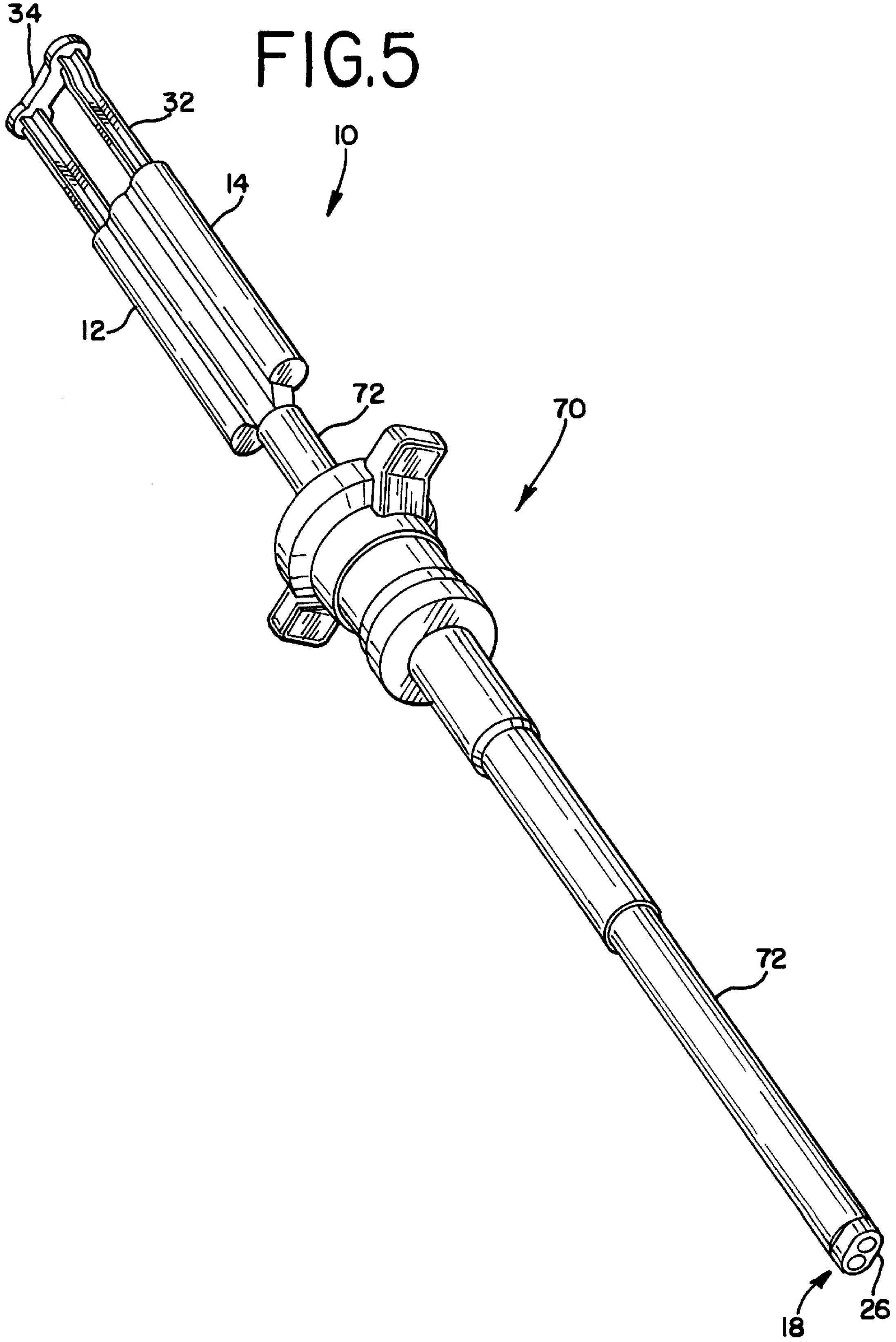
FIG. 5 is a perspective view of the device of the present invention for use in minimally invasive surgical techniques.

FIG. 5 shows the medical device 10 adapted for use in minimally invasive surgical applications. Device 10 has medical tubings 20 which extend from the first and second containers 12 and 14 through a sleeve 72. The sleeve 72 extends through a trocar 70 which is inserted into a surgical opening of an animal body to provide access to a cavity of the animal. In this fashion the spray unit 18 may be directed into the animal cavity to treat a wound therein.

This invention contemplates providing an articulatable joint (not shown) at a distal end of the device 10 which may be controlled by medical personnel outside the animal cavity to position the spray unit 18 to face a wound or surface to be treated with the device 10.

V. Method of Using Device

The medical device 10 of this invention may be used topically, in open-type surgeries (for example, laparotomic surgeries) or minimally invasive surgeries (for example, laparoscopic surgeries). Of course, there are other types of open-type surgeries and minimally invasive as will be appreciated by one of ordinary skill in the art. By mixing the fibrinogen and thrombin outside the device 10, the device may deliver high concentration thrombin solutions without clogging. The medical device 10 may be used to form fibrin films outside the human body using low thrombin concentrations and high thrombin concentrations.

1. Formation of Fibrin Outside Body Using Low Thrombin Concentration

The present invention is also concerned with processes of preparing a self-supporting sheet-like material of cross-linked fibrin.

Accordingly, in certain embodiments of the invention, a process of preparing a self-supporting sheet-like material of cross-linked fibrin is provided, which process comprises the steps of:

(a) simultaneously mixing a stream of a first, fibrinogen-containing solution with a stream of a second, thrombin-containing solution;

(b) applying the obtained mixture to a solid support; and (c) incubating the mixture to form the desired material.

In order to obtain a mixture as homogenous as possible (and thus a homogenous final product) in step (a), a stream of a first, fibrinogen-containing solution is simultaneously mixed with a stream of a second, thrombin-containing solution. The first and/or the second solution may further comprise disinfectants and/or drugs selected from antibiotics, fibrinolytic agents and biological response modifiers, in particular cytokines and wound repair promoters. Preferably, equal volumes of the first and the second solution are mixed. In case the different volumes of the first and the second solution should be simultaneously mixed, it will be known in the art which measures have to be taken in order to ensure that a homogenous mixture is obtained.

Using the delivery device described above, the resulting mixture is spread over the surface of a solid support, for example a petri dish and the like, which is tilted to cover the entire surface as far as possible before the formation of the three-dimensional fibrin network starts. Using this preparation mode, fibrin films made with low concentrations of thrombin can easily be obtained. With higher concentrations of thrombin, a faster clotting time and thus a rapidly increasing viscosity of the mixture are observed as main limitations for the mixing procedure described above. Accordingly, for higher thrombin concentrations, care has to be taken that the mixture formed in accordance with step (a) is uniformly distributed over the surface of the solid support from the beginning, so as to yield a homogenous final product in step (c).

Step (c) preferably requires that the mixture applied to the solid support is allowed to set completely, i.e., a conversion of fibrinogen to fibrin as complete as possible is obtained. Preferably, completion of the conversion of fibrinogen to fibrin is achieved by incubation of the solid support at the physiological temperature, i.e., 37° C., for 1–200 minutes. It will be appreciated that the incubation may also be extended up to 24 hours and more. In this respect it is noted that the invention shall also cover those products, where the fibrinogen to fibrin conversion has not reached completion.

2. Formation of Fibrin Outside Body Using High Thrombin Concentration

As an alternative, in particular for the purpose of preparing a fibrin film with a higher concentration of thrombin, the inventors propose a process comprising the steps of:

(a) applying a first, aqueous, fibrinogen-containing solution onto a solid support;

(b) removing the water until dryness while forming a sheet-like fibrinogen material;

(c) applying to the sheet-like fibrinogen material a second, thrombin-containing solution; and (d) incubating to form the desired material.

Whereas the specific steps of this process differ from those of the previously described process for the preparation of a fibrin film, the same first and second solutions may be used. In a preferred embodiment of said process, equal volumes of the first and the second solution are used in steps (a) and (c).

In order to obtain a final product having a regular thickness and a homogenous structure the first, aqueous, fibrinogen-containing solution should be uniformly distributed over the entire solid support. Step (b) requires that the solvent of the first solution, i.e. water, is removed until dryness in order to obtain a sheet-like fibrinogen material. Preferably, removal of water is performed by air drying, freeze drying, or drying under increased temperature and/or reduced pressure. The obtained sheet-like fibrinogen material has microcavities as shown by SEM and, thus, a high absorptive capacity for fluids. Said material is converted into a self-supporting sheet-like material of cross-linked fibrin upon rehydration by means of the addition of a second, thrombin-containing solution, which optionally comprises disinfectants and/or drugs like antibiotics, fibrinolytic agents, biological response modifiers and the like.

According to step (d), the solid support and, thus, the intermediate product of step (c), is incubated to form the self-supporting sheet-like material of cross-linked fibrin, i.e. the final product. Preferably, step (d) comprises incubating the solid support at 37° C. for about 20 minutes (with material of low thickness) to about 200 minutes (with material of high thickness) to complete the conversion of fibrinogen to fibrin. It will be appreciated that the incubation to form the final product may be extended to up to 24 hours and more.

It has been found that, with this process, the thickness of the fibrin film is independent of the concentration of the thrombin solution used. The fibrin film obtained has a high mechanical strength and can be cut, bent, rolled and sutured, and has a regular surface. In terms of the process, a particular advantage resides in that it is not dependent on the clotting time. That is, no premature clotting may occur, since the first and the second solution are separately applied to the solid support.

It is, of course, recognized that the preliminary process steps of the two processes described above are preferred laboratory procedures that might be readily replaced with other procedures of equivalent effect.

3. Open-type surgeries and topical application

In open-type surgeries, and in topical applications, the spray unit 18 of the device 10 shown in FIG. 4, is positioned facing a surface such as a wound or a surface proximate the wound. The first and second containers 12 and 14 are consecutively or simultaneously pressurized to deliver to the surface the thrombin and the fibrinogen for mixing on the surface. Preferably the thrombin has a concentration from 3–10,000 IU/ml.

4. Minimally Invasive Surgeries

In minimally invasive surgical applications, the invention provides a method for delivering fibrin to a surface to be treated of an animal, or to isolate one surface from another, to prevent the formation of adhesions. The method comprises the steps of: (1) providing a liquid solution of fibrinogen; (2) providing a liquid solution of thrombin having a concentration from 3–10,000 IU/ml and more preferably from 200–500 IU/ml; (3) providing a spray unit in fluid communication with the fibrinogen and thrombin solutions, the spray unit being capable of separately atomizing the fibrinogen and the thrombin into an aerosol with an energy selected from the group consisting of liquid energy, mechanical energy, vibration energy, and electric energy; (4) spraying the fibrinogen solution onto the surface with the spray unit; (5) spraying the thrombin solution separately from the fibrinogen solution onto the surface; and (6) mixing for the first time the fibrinogen with the thrombin on the surface to make a fibrin film, in situ. The film is capable of preventing the formation of adhesions proximate the fibrin film. The trocar 70 and sheathe 72, described above and shown in FIG. 5, may be used to provide access to the animal cavity.

VI. Use of Fibrin Film

Generally speaking, the main determinants in influencing the fibrin network structure and its biological and biophysical characteristics include the concentrations of thrombin, fibrinogen and factor XIII, and, of course, the temperature at which the polymerization is performed. The fibrinogen concentration and, in a large measure, the clottable protein concentration is proportional to the tensile strength, while the concentration of factor XIIIa which covalently crosslinks the fibrin monomers influences the elasticity of the fibrin network.

However, the thrombin concentration plays a key function for controlling fibrin network formation. That is, the biopolymer structure is inversely related to the thrombin concentration, while keeping the same regular and uniform structure at each concentration of thrombin. At low concentrations of thrombin, there is a slow fibrinogen conversion associated with a slow fiber growth, thus leading to the formation of a fibrin structure with thick fibers and large pore size (typically greater than 1 $\mu$m and most preferably greater than 20 $\mu$m). In other words, a low thrombin concentration leads to a long clotting time and larger pores. On the other hand, high concentrations of thrombin result in shorter clotting times producing a tight material with thinner fibrin fibers and smaller pore size (most preferably <1 $\mu$m and more preferably less than 0.2 $\mu$m). This effect can be demonstrated by using standard scanning electron microscopy (SEM). While FIG. 6 shows the network of a fibrin film developed with a low thrombin concentration (3 IU) having a pore size of greater than 1 $\mu$m (about 3–4 $\mu$m), FIG. 7 shows a fibrin film made with a high thrombin concentration (300 IU) having a pore size below 1 $\mu$m (about 0.2 $\mu$m). For comparison, FIG. 8 shows a representative human fibrin clot structure. In the human hemostatic clot, the presence of cells drastically opens the three-dimensional structure of the network. Such an opened and irregular structure is physiologically favorable to fibroblast migration into the fibrin clot network during the normal wound healing process. It is apparent from the figures that by varying the thrombin concentration, fibrin networks with low or high pore size are obtainable. For the use of the fibrin material as a biomechanical barrier in accordance with the present invention, the thrombin concentration is preferably adjusted to obtain a fibrin network structure with a pore size excluding fibroblast penetration. The fibrin material produced in accordance with the invention may be examined by standard SEM and further be tested in the animal model described herein.

In view of these findings, the inventors propose that a fibrin film with a highly ordered structure having a "low pore size" is useful as a biomechanical barrier to avoid contacts between adjacent injured surfaces. Additionally, it is proposed to use a fibrin film with a highly ordered structure having "relatively large pores" as a matrix for cells and molecules for the achievement of hemostasis and wound repair.

This is all the more important as the inventors using the animal model described below, have found that the development of adhesion requires blood, peritoneal trauma, and approximation/contact of injured surfaces.

Under consideration of these three factors, in certain embodiments hemostasis and wound repair is addressed by applying a single layer of fibrin glue to the injury site(s), while the separation/isolation of the injured surface(s) is achieved by using a bio-mechanical fibrin barrier, either applied as a second layer on top of the first layer of the fibrin glue, or simply as a self-supporting sheet placed between the adjacent injury sites or between the site of the injury and the adjacent uninjured tissues. The inventors have discovered that an important parameter to be taken into account in using such a combination of a hemostatic agent/wound repair promoter and a bio-mechanical barrier is the time required for complete conversion of fibrinogen to fibrin. Specifically, it has been found that the layer of the fibrin glue and respectively the last layer, if more than one layer is applied to an injured surface, should be allowed to set until the conversion of fibrinogen to fibrin is complete. By way of example, when fibrin glue is applied simultaneously to two injured surfaces such as caecum and peritoneal wall in order to form a single layer each time, and the surfaces come into contact with each other before the fibrinogen-fibrin conversion is complete, it may occur that these surfaces are glued together, i.e., that adhesions are formed.

This means that the surface state of the different interfaces and their relationships are very important in the prevention of adhesions. As a general guidance, the inventors propose to allow undisturbed setting after application of the respective last external layer of fibrin glue until the conversion of fibrinogen to fibrin is complete. This does not apply to the fibrin film of the invention, since this is allowed to set completely in vitro before application. Of course, although detailed experimental protocols are described hereinafter, those of skill in the art will appreciate that the specific time requirements may vary depending on the particular patient, the type of injury and the handling, and is thus apparently also a matter of clinical experience. However, in vitro methods are known in the art for monitoring the fibrinogen-fibrin conversion. By way of example this can be followed by monitoring turbidity which is the measure of the optical density of fibrin networks developed in a cuvette with a path of one centimeter at 800 nm (cf. G. A. Shah et al., *Thrombosis Research* 40, 818–188, 1985). In accordance with this method it is possible to determine in vitro the time required for complete fibrin formation at a given thrombin concentration. This provides an estimate of the minimum time required for complete setting after application of the last external layer(s). It is believed that, based on the present disclosure, one of ordinary skill in the art could define a protocol for use of a dedicated fibrin glue, its mode and type of application, so that the requirements for surgeons with respect to the timing and the technical devices are met.

In accordance with the general guidelines described above, a preferred embodiment called "double coating" comprises the application of a first fibrin glue with a low concentration of thrombin to work as hemostatic agent and/or tissue repair promoter, and of a second fibrin glue with a high concentration of thrombin playing the role of a bio-mechanical barrier which entirely covers the injury and the first coating formed upon application of the first fibrin glue. Preferably the first fibrin glue has been made by mixing of the above-described fibrinogen-containing solution with an equal volume or a thrombin-containing solution comprising less than 1000 IU thrombin, preferably less than 150 IU. The fibrin glue has been preferably made by mixing said fibrinogen-containing solution with an equal volume of a thrombin-containing solution of at least 50 IU thrombin, preferably of at least 150 IU thrombin, and most preferably of least 300 IU thrombin. Of course, it will also be possible to apply more than two layers as long as the last layer plays the role as a biomechanical barrier preventing fibroblast proliferation between the covered lesion and the adjacent surfaces.

In another preferred embodiment of the invention called "sandwich method," a fibrin glue layer covering the injured surface(s) is used as hemostatic agent and wound repair promoter, while a fibrin film, in i.e., a self-supporting sheet-like material of cross-linked fibrin being placed between the injured surface and an adjacent uninjured surface, or between two injured surfaces, acts as a biomechanical barrier. The fibrin glue is preferably produced by mixing of a first, fibrinogen-containing solution with an equal volume of a thrombin-containing solution comprising preferably 1–300 IU/ml thrombin, preferably at least 20 IU/ml thrombin and most preferably at least 100 IU/ml thrombin. The fibrin film is made of at least 4 IU/ml thrombin, preferably of at least 20 IU/ml thrombin, and most preferably of at least 300 IU/ml thrombin. It will, of course, be recognized that the fibrin film can also be used in combination with a double coating as described above.

The above-described embodiments may be used either alone or in combination with other embodiments.

VII. Hemostasis and Antiadhesion Purposes

The device 10 and the methods described above for using the device, are effective for both hemostasis and antiadhesion purposes. For hemostasis, it is preferable to apply a thrombin solution having a thrombin concentration of less than 400 IU/ml and more preferably from 1–10 IU/ml. The application of both fibrinogen and thrombin are even effective in high blood flow applications.

For antiadhesion purposes, it is preferable to use a thrombin concentration of from about 10–10,000 IU/ml and more preferably from 200–500 IU/ml. The biochemically reactive fluids are applied to a surface such as a wound or neighboring tissue to form a fibrin film capable of isolating tissues from healing tissues.

VIII. Sequential and Simultaneous Pressurization

As stated above, it is possible to deliver the thrombin and the fibrinogen sequentially or simultaneously. In simultaneous applications, the fibrinogen and thrombin are applied in amounts sufficient to have the desired function of hemostasis or of forming a fibrin film of sufficient thickness to act as a barrier.

In sequential applications, the fibrinogen and thrombin may be applied in either order but preferably the thrombin is sprayed on first followed by the fibrinogen. To form a fibrin film for antiadhesion purposes having a uniform and regular surface, it is preferred that the fibrin film be formed incrementally. This incremental approach requires spraying small volumes, such as 0.3 ml or any volume that may be somewhat accurately measured using a syringe, of each of the biochemically reactive fluids onto the surface and repeating this process until the fibrin film has a desired thickness. This process may have to be repeated from about 1–5 times to form a fibrin film having a thickness of say about 500 $\mu$m. This incremental process overcomes the natural tendency for the later sprayed fluid to displace the earlier sprayed fluid creating an irregular surface in the fibrin film. By spraying small fluid volumes the fluid displacement is minimized.

IX. Materials and Methods 1.1 Animals

For these studies, female Wistar rats weighing 180–200 g each were used. Before surgery the animals were kept in groups in cages and after surgery until necropsy they were kept alone. The strain designation is ICO.WI/(IOPS, CPB). The experiments were performed following the guidelines of the "Législation et réglementation relative á l'expérimentation animale."

1.2 Materials

For these experiments, Baxter Fibrin Sealants kits lot # 26302001AA were used. While these kits are not on the market yet, in the light of the present disclosure any standard two-component fibrin sealant kit may be used for the purposes of the invention.

Calcium Chloride 20 mM from Nycomed lot# 931343 Petri dish (9 cm diameter) from Nunc (cell culture quality) were used.

1.3 Surgical and Anaesthetic Equipment

The surgical equipment included: PVC plate (surgery table) 30×30 cm; needle holders CRILE-WOOD, 14 cm; forceps; Wangesteen, 15 cm; standard anatomic forceps, 13 cm; dissecting scissors, Metzenbaum, 14 cm; home-made clamp (for fixing a tissue surface of 2 $cm^2$); lamp, Well-Lynch; scalpels SWANN-MORTON disposable # 24; surgical suture USP Dermalon non-absorbable, Dermalon 2.0 needle CE-4, Dermalon 4.0 needle CE-6; gauze swabs: layer 12, 10×10 cm Molnlycke. Diethyl ether was used as anaesthetic.

The home-made clamp shown in FIG. 12 serves as a tool to standardize the injuries inflicted on the surface of the parietal wall in terms of their position, area and depth. The clamp consists of two mobile parts. The "male" part has rounded edges and embraces an area of 2 $cm^2$ corresponding to the surface of the smallest caecum found in a rat. When the clamp is closed, there is a gap of 2 mm between the male and the female part, which gap is sufficient to keep the respective tissue (muscle layer, skin) immobile without any shearing or cutting. The mechanical tension induced by the clamp is necessary to allow easy separation of the first muscle layer from the second one when the clamped surface is incised with a scalpel. The tension allows better control of the depth of incision.

1.4 Disinfection and Biological Waste

Surgery equipment was disinfected and washed with 15–20 g/l Mucocit-R (Merz) as per the technical data sheet. For all materials as well as the dead animal carcasses, usual measures for waste disposal were taken.

1.5 Animal Surgery

The surgical procedure as described below, using the above-described clamp, allows production of adhesions of the same type in control experiments with an incidence of 100 percent.

The skin was cut following a 4 cm line joining the xyphoid and urinary aperture for a rat weighing 180–200 g with a pair of Metzenbaum scissors.

The skin edges were lifted and carefully dissected from the muscle wall on each side of the linea alba.

The abdominal muscle was incised along the linea alba over the 4 cm line as described above.

The caecum was gently removed and laid on gauze swab avoiding, at any time, contact with the latex gloves and damage by instruments.

The caecum was abraded with gauze on its upper side until only punctuate bleeding appeared.

The caecum was returned to the peritoneal cavity if no treatment had to be performed. If a treatment was carried out, the product to be tested was applied on the caecum, which was then gently returned to the peritoneal cavity.

In the next step, the home-made clamp described above was used which had been designed to standardize the injury inflicted on the parietal wall in terms of area, position and depth, thus duced. Then the clamp was turned inside out to expose the parietal wall.

The exposed serosal surface was incised through the first muscular layer with 2×10 crossed incisions of constant depth.

After this step, the incised surface was replaced on the abraded caecum if no treatment had to be performed. If a treatment was performed, the product was applied on the incised surface and then carefully replaced on the abraded caecum such that caecum and parietal wall were separated by the product.

At that time, care was taken to avoid any movement that could induce distension or stretching, especially to the parietal caecum side.

The muscle was sutured with non-absorbable dermalon 2.0 and the skin closed with dermalon 4.0.

The animal identification was performed by using an electronic tag (ZETES Electronic Inc.) defined by an univocal key of 12 alpha-numeric digits.

Then the animals were allowed to recover in the laboratory.

1.6 Sham Control

A "Sham" was performed by following all the steps of the surgical procedure, but without inflicting incisions or abrasions. Surgery timing was rigorously observed.

1.7 Animal Sacrifice

The animals were sacrificed after 10 days. The post-mortem viscera studies were made through a U-shaped abdominal incision started at the liver level. Adhesions, present in the peritoneal cavity, were evaluated by two independent investigators.

1.8 Adhesion Classification

The adhesions were recorded according to their nature and tensile characteristics.

1.8.1 Nature of the Adhesion

The adhesions were classified in a table depending on the organs involved in the adhesion process. The adhesions involving the sutures were recorded, but will not be listed as adhesions hereinafter.

The main adhesion type observed and classified are:

caecum/parietal visceral/visceral fat/parietal fat/visceral fat/fat

The name of the fat or viscera in relationship with the "nature of the adhesion" will also be mentioned in parentheses.

e.g.: grade 2 adhesion between the fat of the uterus and the parietal wall will be reported as follows:

fat/par (Ut) (2)

Ovary (O), Colon (Co), Ileum (Il), Bladder (Bl), and Omentum (Om) may also be involved in the adhesion process.

1.8.2 Tensile Characteristics

The adhesion was pealed off and evaluated according to the macromorphological adhesion grading scale (MAS) as follows:

0: no adhesion

1: filmy (mild)

2: adhesive bands (medium)

3: extensive adhesion formation (severe)

The adhesion tensile value was recorded in the appropriate column of the respective table with the type of organ involved in the adhesion process, as described above.

1.9 Type of Application

Two different types of application were performed with fibrin glue (FG): a "single coating" (one layer) or a "double coating" (two layers).

1.9.1 Single Coating

A fibrin glue with a defined thrombin concentration was used as an hemostatic agent and tissue repair promoter, respectively.

Fibrin glue was applied as a "single coating" on the caecum and the parietal wall as described in paragraph 1.5.

1.9.2 Double Coating

Two fibrin glues, at two different concentrations of thrombin, a low and a high, were used.

The fibrin glue having the low thrombin concentration was used as a first layer of the double coating.

The fibrin glue having the high thrombin concentration, applied as "second layer," plays the role of mechanical barrier which entirely covers the injury and the first layer. The kinetic of fibrin formation of the second layer is faster than that of the first one and also the physical properties of the two layers are different.

1.10 Mode of Application

Caecum was abraded and the parietal wall was incised, respectively, and covered with a single or a double coating of fibrin glue (FG) depending on the protocol design.

Fibrin glue can be applied sequentially or simultaneously on both injured surfaces.

By combining the application type (single or double) and the application mode (sequential or simultaneous), four different cases can be obtained (cf. FIG. 5).

Case 1 single coating & sequential application

Case 2 double coating & sequential application

Case 3 single coating & simultaneous application

Case 4 double coating & simultaneous application (Case 2 will not be tested herein. Case 3 represents the "in vivo" conditions for the adhesion development.)

2. EXAMPLES

Example 1

Preparation of a Fibrin Film Using a Dual Syringe Device

The fibrin films were casted by using a commercial dual syringe device, not of the present invention, after reconstitution of the vials of a commercial fibrin glue kit in accordance with the information in the instruction leaflet of the respective kit employed. By way of example, a two-component fibrin glue kit comprising the following constituents may be used:

| | | |
|---|---|---|
| Vial (1) | Human topical fibrinogen complex (dry concentrate) | |
| | protein | 10–13 g/100 ml |
| | clottable protein | 80% minimum |
| | albumin (human) | 0.5–1.5 g/100 ml |
| | plasminogen | 0.05 mg/ml maximum |
| | Factor XIII | 10–40 IU/ml |
| | polysorbate-80 | 0.3% (w/v) maximum |
| | pH | 7.1–7.5 |
| Vial (2) | Sterile water (3.5 ml) for reconstituting the content of vial (1) at 37° C. in a water bath | |
| Vial (3) | Human thrombin | |
| | potency | 300 + 50 IU/ml |
| | albumin (human) | 0.05 + 0.01 g/ml |
| | glycine | 0.30M + 0.05M |
| | pH | 6.5–7.1 |
| Vial (4) | 35–45 mM $CaCl_2$ (3.5 ml) for reconstituting the content of vial (3) at room temperature | |

After reconstitution, the fibrinogen-containing solution was kept at room temperature. Further thrombin dilutions were made with 20 mM $CaCl_2$ as diluent. Using the dual syringe device, not of the present invention, the mixture "Fibrinogen-Thrombin" was applied to a petri dish, while care was taken that at any time equal amounts of the fibrinogen-containing solution and the thrombin-containing solution were pressed out of the respective syringe. With low concentrations of thrombin, the petri dish was tilted to cover the surface with a fibrin glue of regular and homogenous thickness. With high concentrations of thrombin, particular care was taken that from the beginning the mixture of the fibrinogen-containing solution and the thrombin-containing solution was uniformly spread over the surface of the petri dish. The petri dish was incubated at 37° C. for two hours.

Optionally, disinfectants, e.g. methylene blue in a concentration of 10 mg/l–10 g/l or drugs, may be dissolved in the contents of vials (2) or (4) before these are used for reconstituting the contents of vials (1) and (2), respectively.

The Fibrin film obtained may be air-dried and rehydrated before use. If the thrombin solution did not already comprise substances, like disinfectants or drugs for enhancing the desired therapeutic effect on the fibrin film, the solution used for rehydration may include those substances.

Example 2

Preparation of a Fibrin Film Using a Dry Fibrinogen Sheet

The solutions given in Example 1 were used with the following modifications.

3.5 ml of the reconstituted fibrinogen-containing solution were poured in a petri dish of 51 mm diameter which was tilted to spread the material all over the entire surface. The water contained in the fibrinogen-containing solution was evaporated by air drying. Thus, a dry fibrinogen sheet having a thickness of 100 $\mu$m and a weight of 0.4291 g was obtained. 3.5 ml of a reconstituted thrombin-containing solution were poured into the petri dish containing the dry, sheet-like fibrinogen material. The reaction mixture was then kept at 37° C. for 2 hours. The fibrin film thus obtained may either directly be used or be dried and rehydrated before use. Alternatively, the dry, sheet-like fibrinogen material may be converted into a fibrin film only before use.

Both the dry, sheet-like fibrinogen material and the dried fibrin film may be included in a commercial kit further comprising ancillary components for processing and rehydration, respectively, of the sheet-like materials.

Example 3

Preparation of a Fibrin Sealant/Glue

The preparation of a fibrin glue was performed as per the technical information of the instruction leaflet provided with the kit employed. The fibrin glue was prepared extemporaneously at different concentrations of thrombin, e.g. 4, 5, 20, 100, 150, and 300 IU/ml and used as described hereinbelow.

Example 4

"Control" Group

The animals were operated to develop adhesion, and therefore no treatment had been carried out. Accordingly, hemostasis was not achieved, and, thus, all conditions to develop with an incidence of 100% severe type 3 adhesions between the caecum and the parietal wall were present.

The results are reported in the following Table 1:

TABLE 1

Control Group

| No.* | Products Applied | Adhesion Par. & Caec. | Visc. & Caec. | Fat & Caec. | Fat & Pariet |
|---|---|---|---|---|---|
| 1 | ————————/——————/————————— | (3) | (Ut) (1) | — | — |
| 2 | ————————/——————/————————— | (3) | — | (Ut) (1) | (Om) (1) |
| 3 | ————————/——————/————————— | (3) (xx) | — | — | — |
| 4 | ————————/——————/————————— | (3) | — | (Ut) (1) | (Ut) (1) |
| 5 | ————————/——————/————————— | (3) (xx) | — | — | — |
| 6 | ————————/——————/————————— | (3) (xx) | — | — | — |
| 7 | ————————/——————/————————— | (3) | — | — | — |
| 8 | ————————/——————/————————— | (3) (xx) | — | — | — |
| 9 | ————————/——————/————————— | (3) | — | — | — |
| 10 | ————————/——————/————————— | (3) | — | — | (B1) (1) |
| 11 | ————————/——————/————————— | (3) | — | — | — |
| 12 | ————————/——————/————————— | (3) | — | — | (Om) (1) |
| 13 | ————————/——————/————————— | (3) | — | — | — |
| 14 | ————————/——————/————————— | (3) | — | (Om) (1) | (Om, Ut) (1, 1) |
| 15 | ————————/——————/————————— | (3) | — | — | — |
| 16 | ————————/——————/————————— | (3) | — | — | — |
| 17 | ————————/——————/————————— | (3) | — | — | — |
| 18 | ————————/——————/————————— | (3) | — | — | — |
| 19 | ————————/——————/————————— | (3) | — | — | — |
| 20 | ————————/——————/————————— | (3) | — | — | — |
| 21 | ————————/——————/————————— | (3) | — | — | — |

* = Number of animal (female Wistar rat)
(x) = a piece of fibrin was still present No adhesions were observed with both animals. The results are reported in the following Table 2:

TABLE 2

Sham Control with Fibrin Film

| No.* | Product Applied | Adhesion Pat. & Caec. | Visc. & Caec. | Fat & Caec. | Fat & Pariet. | Fat & Visc. | Fat & Fat |
|---|---|---|---|---|---|---|---|
| 1 | SHAM (FF 20 IU) | — | — | — | — | — | — |
| 2 | SHAM (FF 3 IU) | — | — | — | — | — | — |

*= Number or animal (female Wistar rat)

Example 5

Fibrin Film Application

As a rule the fibrin films used were made in accordance with Example 1.

Example 5a

Sham Control with Fibrin Film (FF)

Two animals were used as sham control. One received a fibrin film made using 3 IU thrombin and with water as diluent (FF 3 IU), the other received fibrin film made using 20 IU thrombin and with 20 mM $CaCl_2$ as diluent (FF 20 IU). No injuries were induced on the caecum and peritoneum.

Example 5b

Application of a Fibrin Film without Control of Hemostasis

Fibrin films FF 3 IU and FF 20 IU in accordance with Example 5a were used as mechanical barrier without controlling hemostasis on the caecum and parietal injuries. Alternatively, a Fibrin Film 300 IU was used as mechanical barrier.

The animal sacrificed after 10 days showed medium caeco-parietal adhesions (type 2) and large number of fat adhesions, involving mainly uterus and bladder. Surprisingly and most importantly, the animals treated with FF 300 IU virtually did not develop any adhesions.

The results are reported in the following Table 3:

TABLE 3

| | | Fibrin Film Alone | | | | | |
|---|---|---|---|---|---|---|---|
| | | Adhesion | | | | | |
| No.* | Product Applied | Pat. & Caec. | Visc. & Caec. | Fat & Caec. | Fat & Pariet. | Fat & Visc. | Fat & Fat |
| 1 | SHAM (FF 20 IU) | —° | —° | —° | —° | —° | —° |
| 2 | SHAM (FF 3 IU) | —° | —° | —° | —° | —° | —° |
| 3 | FF 3 IU | — | — | (UT) (2) | (Ut, Bl) (3,2) | — | — |
| 4 | FF 3 IU | (2) | — | (Om, Ut) Bl) (2, 2,2) | (Om) (2) | — | — |
| 5 | FF 3 | (2) | — | (Ut) (2) | — | — | — |
| 6 | FF 3 | (1) | — | (Ut, Bl) (2,2) | (Ut) (2) | — | — |
| 7 | FF 20 IU | (2) | — | (Ut) (2) | (Ut(2) | — | — |
| 8 | FF 20 IU | (3) | — | — | — | — | — |
| 9 | FF 20 IU | (3) | — | (Ut) (1) | — | — | — |
| 10 | FF 20 IU | (1) | — | — | — | — | — |
| 11 | FF 300 IU | — | — | — | — | — | — |
| 12 | FF 300 IU | — | — | (Ut) (1) | — | — | — |
| 13 | FF 300 IU | — | — | — | — | — | — |
| 14 | FF 300 IU | — | — | — | — | — | — |

*= Number of animal (female Wistar rat)
°= Necropsy after 3 days/others after 10 days The fibrin film in accordance with the invention which was used for the treatment of animal no. 11 was obtained by an alternative process as follows:

The first, fibrinogen-containing solution was poured in a petri dish having a diameter of 91 mm. The temperature of said solution was decreased by incubating the petri dish for a few minutes at low temperature, here for 4 min. at −12° C. Then the second, thrombin-containing solution (RT) was added and mixed with the first solution. The petri dish was incubated until completion of the conversion of fibrinogen to fibrin, here for 24 hours at 37° C.

Example 6

Fibrin Glue "Single Coating"

Using thrombin-containing solutions comprising 4 IU/ml (cf. Example 6a) and 100 IU/ml thrombin (cf. Example 6b), fibrin glues were applied as hemostatic agent to the abraded caecum and the incised peritoneum each. By way of example, this is shown in the following Table as follows: FG 4 IU / - - - - / FG 4 IU; where (- - - -) indicates that no fibrin film is placed between the injuries. The fibrin glue was applied to the injuries in sequence. The waiting time to allow a setting of the fibrin glue was 5 minutes after each application.

In Example 6a, severe type 3 adhesions between the caecum and the parietal wall were observed.

The results are shown in the following Table 4:

TABLE 4

| | Single Coating, Sequential Application Time: 5 min | | | | |
|---|---|---|---|---|---|
| | | Adhesion | | | |
| No.* | Products Applied | Par. & Caec. | Visc. & Caec. | Fat & Caec. | Fat & Pariet. |
| 1 | FG 4 IU / - - - -/ FG 4 IU / - - - -/ | (3) | — | — | — |
| 2 | FG 4 IU / - - - -/ FG 4 IU / - - - -/ | (2) | — | — | — |
| 3 | FG 4 IU / - - - -/ FG 4 IU / - - - -/ | (3) | — | — | — |
| 4 | FG 4 IU / - - - -/ FG 4 IU / - - - -/ | (3) | — | — | — |
| 5 | FG 4 IU / - - - -/ FG 4 IU / - - - -/ | (3) | — | — | — |

*= Number of animal (female Wistar rat)

In Example 6b, two animals developed severe type 3 adhesions between caecum and parietal wall. The caecum was partly included into the parietal wall. Two animals did not develop adhesion.

The results are reported in the following Table 5:

TABLE 5

| | Single Coating, Sequential Application Time: 5 min | | | | |
|---|---|---|---|---|---|
| | | Adhesion | | | |
| No.* | Products Applied | Par. & Caec. | Visc. & Caec. | Fat & Caec. | Fat & Pariet. |
| 1 | FG 100 IU / - - - -/ FG 100 IU / - - - -/ | (3) | — | — | (Om, Ut) (1, 1) |
| 2 | FG 100 IU / - - - -/ FG 100 IU / - - - -/ | — | — | — | — |
| 3 | FG 100 IU / - - - -/ FG 100 IU / - - - -/ | — | — | — | — |
| 4 | FG 100 IU / - - - -/ FG 100 IU / - - - -/ | (3) | — | — | — |

*= Number of animal (female Wistar rat)

Example 7

Fibrin Glue "Double Coatings"

Fibrin glues were applied at two different thrombin concentrations.

Example 7a

A first layer of a fibrin glue made using a thrombin-containing solution comprising 4 IU/ml thrombin (-G 4 IU) was simultaneously (i.e., only with a minimal delay caused by the handling) applied to both the abraded caecum and the incised parietal wall.

After a waiting time of 5 minutes to allow the polymerization, a second layer of fibrin glue 100 IU, FG 100 IU, was simultaneously applied on the same organs. This was followed by a second waiting time of 5 minutes before the surgical procedure was continued.

One animal did not develop adhesion. With one animal, which developed a severe type 3 adhesion, a remaining piece of fibrin was observed. Three animals developed mild type 1 adhesions between the caecum and the parietal wall.

The results are reported in the following Table 6:

TABLE 6

Double coating with FG 4 IU and FG 100 UL, Simultaneous Application Time: 5 Minutes

| No.* | Products Applied | Adhesion Par. & Caec. | Visc. & Caec. | Fat & Caec. | Fat & Pariet. |
|---|---|---|---|---|---|
| 1 | FG 4 & 100 IU / - - - -/ FG 4 & 100 IU / - - - -/ | (3) (x) | — | — | (Om, Ut) (1,1) |
| 2 | FG 4 & 100 IU / - - - -/ FG 4 & 100 IU / - - - -/ | (1) | — | — | — |
| 3 | FG 4 & 100 IU / - - - -/ FG 4 & 100 IU / - - - -/ | (1) | — | — | — |
| 4 | FG 4 & 100 IU / - - - -/ FG 4 & 100 IU / - - - -/ | — | — | — | — |
| 5 | FG 4 & 100 IU / - - - -/ FG 4 & 100 IU / - - - -/ | (1) | — | — | — |

*= Number of animal (female Wistar rat)
x= a piece of fibrin was still present

Example 7b

A parallel experiment under the same conditions was conducted, but with the single exception that higher thrombin concentrations (FG 5 IU and FG 150 IU) were used.

Four animals did not develop adhesion. With one animal, which developed a mild type 2 adhesion between the caecum and the parietal wall, a remaining piece of fibrin was observed.

The results are reported in the following Table 7:

TABLE 7

Double coating with FG 5 IU and FG 150 UL, Simultaneous Application Time: 5 Minutes

| No.* | Products Applied | Adhesion Par. & Caec. | Visc. & Caec. | Fat & Caec. | Fat & Pariet. |
|---|---|---|---|---|---|
| 1 | FG 5 & 150 IU / - - - -/ FG 5 & 150 IU / - - - -/ | (2) (x) | — | — | — |
| 2 | FG 5 & 150 IU / - - - -/ FG 5 & 150 IU / - - - -/ | — | — | — | — |
| 3 | FG 5 & 150 IU / - - - -/ FG 5 & 150 IU / - - - -/ | — | — | — | — |
| 4 | FG 5 & 150 IU / - - - -/ FG 5 & 150 IU / - - - -/ | — | — | — | — |

*= Number of animal (female Wistar rat)
x= a piece of fibrin was still present

Example 8

Sandwich Method—Use of a Combination of a Fibrin Glue and a Fibrin Film

The sandwich method combines the use of a fibrin glue as hemostatic agent/wound repair promoter and of a fibrin film as mechanical barrier. Three types of fibrin film which had been made using 4 IU, 20 IU and 300 IU thrombin in accordance with Example 1 were used. Due to the different thrombin concentrations of the respective fibrin films, the time required for complete fibrinogen-fibrin conversion varied. However, this is of no importance as the films were kept at 37° C. for more than two hours, a time greater than that required as determined theoretically and practically by means of turbidity measurement.

Example 8a

A fibrin glue 100 IU used as hemostatic agent was applied simultaneously both to the abraded caecum and the incised parietal wall with a waiting time of 5 minutes. In parallel (cf. (ii)), it was applied sequentially to the abraded caecum and the incised parietal wall with a waiting a time of 7 minutes each time. In both experiments, a fibrin film of 4 IU was used.

(i) Simultaneous application time: 5 minutes

Two animals did not develop adhesions between caecum and parietal wall, while two animals (developed mild type 1 adhesions between these surfaces. One animal developed a type 2 caeco-parietal adhesion.

The results are reported in the following Table 8:

TABLE 8

Sandwich Method, Simultaneous Application Time: 5 Minutes

| No.* | Products Applied | Adhesion Par. & Caec. | Visc. & Caec. | Fat & Caec. | Fat & Pariet. |
|---|---|---|---|---|---|
| 1 | FG 100 IU / - - - -/ FG 100 IU / - - - -/ | — | (Ut(1) | — | — |
| 2 | FG 100 IU / - - - -/ FG 100 IU / - - - -/ | (1) | — | — | — |
| 3 | FG 100 IU / - - - -/ FG 100 IU / - - - -/ | (1) | — | — | — |
| 4 | FG 100 IU / - - - -/ FG 100 IU / - - - -/ | — | — | — | — |
| 5 | FG 100 IU / - - - -/ FG 100 IU / - - - -/ | (1) | — | — | — |

*= Number of animal (female Wistar rat)

(ii) Sequential application time: 7 minutes

Virtually none of the animals developed adhesion. The results are reported in the following Table 9:

TABLE 9

Sandwich Method, Sequential Application Time: 7 Minutes

| No.* | Products Applied | Adhesion Par. & Caec. | Visc. & Caec. | Fat & Caec. | Fat & Pariet. |
|---|---|---|---|---|---|
| 1 | FG 100 IU/FF 4 IU/ FG 100 IU | — | — | — | — |
| 2 | FG 100 IU/FF 4 IU/ FG 100 IU | — | — | — | — |
| 3 | FG 100 IU/FF 4 IU/ FG 100 IU | — | — | — | (Bl) (1) |
| 4 | FG 100 IU/FF 4 IU/ FG 100 IU | — | — | — | — |
| 5 | FG 100 IU/FF 4 IU/ FG 100 IU | — | — | — | — |

*= Number of animal (female Wistar rat)

Example 8b

In another experiment, a fibrin glue 100 IU and a fibrin film 20 IU were used in combination. The fibrin glue was sequentially applied to the abraded caecum and to the incised parietal wall with a waiting time of 7 minutes each.

None of the animals developed adhesion.

The results are reported in the following Table 10:

TABLE 10

Sandwich Method, Sequential Application Time: 7 Minutes

| | | Adhesion | | | |
|---|---|---|---|---|---|
| No.* | Products Applied | Par. & Caec. | Visc. & Caec. | Fat & Caec. | Fat & Pariet. |
| 1 | FG 100 IU/FF 20 IU/ FG 100 IU | — | — | — | — |
| 2 | FG 100 IU/FF 20 IU/ FG 100 IU | — | — | — | — |
| 3 | FG 100 IU/FF 20 IU/ FG 100 IU | — | — | — | — |

*= Number of animal (female Wistar rat)

Example 8c

In a further experiment, a fibrin glue 100 IU was combined with a fibrin film 300 IU. The fibrin film of the invention was obtained in accordance with the alternative method mentioned in Example 5 (cf. animal no. 11), but with an incubation of 10 min. at −12° C. The fibrin film thus obtained was air dried and then rehydrated before being used like a fibrin film made in accordance with Examples 1 and 2. As in Example 8b, the fibrin glue was sequentially applied to the abraded caecum and the incised parietal wall with an application time of 7 minutes each.

One animal developed a very mild adhesion. The other four animals did not develop any adhesions.

The results are summarized in the following Table 11:

TABLE 11

Sandwich Method, Sequential Application Time: 7 Minutes

| | | Adhesion | | | |
|---|---|---|---|---|---|
| No.* | Products Applied | Par. & Caec. | Visc. & Caec. | Fat & Caec. | Fat & Pariet. |
| 1 | FG 100 IU/FF 300 IU(*)/ FG 100 IU | (<1) | — | — | — |
| 2 | FG 100 IU/FF 300 IU(*)/ FG 100 IU | — | — | — | — |
| 3 | FG 100 IU/FF 300 IU(*)/ FG 100 IU | — | — | — | — |
| 4 | FG 100 IU/FF 300 IU(*)/ FG 100 IU | — | — | — | — |
| 5 | FG 100 IU/FF 300 IU(*)/ FG 100 IU | — | — | — | — |

*= Number of animal (female Wistar rat)

Example 8d

In addition, experiments were performed using a fibrin film FG 20 IU in combination with fibrin films of 20 IU and 300 IU, respectively. The fibrin films were made in accordance with Example 1, air-dried and then rehydrated before use. As in Example 8c, the fibrin glue was sequentially applied to the abraded caecum and the incised parietal wall with a waiting time/application time of 7 minutes each.

None of the animals developed any adhesions.

The results are summarized in the following Table 12:

TABLE 12

Sandwich Method, Sequential Application Time: 7 Minutes

| | | Adhesion | | | |
|---|---|---|---|---|---|
| No.* | Products Applied | Par. & Caec. | Visc. & Caec. | Fat & Caec. | Fat & Pariet. |
| 1 | FG 20 IU/FF 20 IU/FG 20 IU | — | — | — | — |
| 2 | FG 20 IU/FF 20 IU/FG 20 IU | — | — | — | — |
| 3 | FG 20 IU/FF 20 IU/FG 20 IU | — | — | — | — |
| 4 | FG 20 IU/FF 20 IU/FG 20 IU | — | — | — | — |

*= Number of animal (female Wistar rat)

3. Discussion 3.1 Application of a Fibrin Film without Control of Hemostasis

As shown in Example 3b, fibrin films made by using 3 IU and 20 IU, if used in an uncontrolled hemostatic environment, did not prevent adhesion formation. On the other hand, the use of fibrin films with high thrombin concentration completely prevented adhesion formation without hemostasis being performed.

3.2 Single Coating

Sequential application of FG 4 IU (cf. Example 6a) did not prevent adhesion formation at all, whereas sequential application of FG 100 IU (cf. Example 6b) allowed a 50% prevention of adhesion formation. These findings suggest that the conversion of fibrinogen to fibrin was not complete on both caecum and parietal wall.

3.3 Double Coating

The simultaneous application of FG 4 & 100 for five minutes was still too short to prevent adhesion formation, but decreased the adhesion grade and tensile properties (cf. Example 7a).

In Example 7b, rather than to increase the simultaneous application time/waiting time for achieving complete fibrinogen-fibrin conversion, the thrombin concentrations were increased in order to reduce the clotting time. In fact, with the simultaneous application of FG 5 & 150 for five minutes, the number of adhesions was decreased.

The presence of a remaining fibrin piece in Examples 7a and 7b indicates, however, that the application volume had to be better controlled. It also has to be pointed out that the double coating of fibrin glues was applied to an injured area where the fibrinolytic system was dramatically impaired. A more controlled delivery (by better handling) and a lower volume of fibrin glue at a higher thrombin concentration (to achieve a faster and more complete conversion of fibrinogen to fibrin) seem to be more suitable for improving the outcome.

3.4 Sandwich Method Using a Fibrin Glue and a Fibrin Film

As shown in Table 8, simultaneous application of FG 100 IU/FF 4 IU/FG 100 IU for five minutes did not totally prevent adhesion formation. The fibrin film made by using 4 IU thrombin is induced a stabilized film having a complete fibrinogen-fibrin conversion, but the inventors are aware that such a fibrin film has particularly large and opened pores. On the other hand, Table 8 shows that FG 100 IU, applied with a waiting time of five minutes, did not completely prevent the development of adhesions. Thus, it may be that FG 100 IU had not reached completion of the conversion of fibrinogen to fibrin and interacted with FF 4 IU in such a manner that no complete prevention of adhesion formation was achieved.

Principally, this could be avoided by either increasing the thrombin concentration of the fibrin glue used (to achieve a faster clotting) or by increasing its sequential application time (to provide more time for the fibrinogen-fibrin conversion), or by increasing the thrombin concentration of the fibrin film (to produce smaller pores).

As shown in Table 9, when increasing the sequential application time up to seven minutes, the application of FG 100 IU/FF 4 IU/FG 100 IU prevented adhesion formation. Likewise, adhesion formation was prevented by increasing the thrombin concentration of the fibrin film to 20 IU as can be taken from Table 10.

It appeared interesting to test a fibrin film made by using a very high thrombin concentration (300 IU). In this case (cf. Table 11), the first coating to control hemostasis (FG 100 IU) as well as application mode and time were maintained in order to compare this situation with the previous examples. In the light of the present disclosure (cf. Table 12), those of skill in the art will appreciate that different combinations may lead to excellent results in the prevention of adhesion formation. Finally, it is pointed out that interestingly the fibrin film FF 300 IU completely prevented adhesion formation without hemostasis having been performed, while this was not achieved by using FF 20 IU. The above-described experiments indicate that with the sandwich technique even fibrin films having a pore size above 5 μm may be used, while the fibrin films preferably should have a pore size below 5 μm when used alone, i.e., without control of hemostasis.

Example 9

Using the Fibrin Delivery Device of the Present Invention

Fibrin Film 1: A fibrin film was formed by simultaneously spraying onto a plastic petri dish 1 ml of a liquid solution of fibrinogen having a concentration of 50 mg/ml and 1 ml of a thrombin concentration of 100 IU/ml. The Fibrin Film upon visual inspection appeared to have a regular, homogenous structure.

Fibrin Film 2: A fibrin film was formed by sequential spraying onto a plastic petri dish a fibrinogen solution having a concentration of 50 mg/ml and a thrombin concentration of 100 IU/ml. The sequential spraying including spraying 1 ml of thrombin followed by 1 ml of fibrinogen. The Fibrin Film upon visual inspection appeared to have a regular, homogenous structure.

While specific embodiments have been illustrated and described, numerous modifications are possible without departing from the spirit of the invention, and the scope of protection is only limited by the scope of the accompanying claims.

We claim:

1. A medical device for laparoscopically delivering volumetric quantities of a first and a second biochemically reactive fluid comprising:

a first container having a first fluid opening, the first container being adapted to contain the first biochemically reactive fluid;

a second container having a second fluid opening adjacent the first fluid opening, the second container being adapted to contain the second biochemically reactive fluid;

means for separately atomizing the first and second biochemically reactive fluids into an aerosol with at least one energy source selected from the group consisting of a liquid energy, a mechanical energy, a vibration energy, and an electric energy;

a fluid pressurizer for pressurizing the first and the second biochemically reactive fluids for delivery under pressure through a spray unit onto a surface; and wherein the first and second biochemically reactive fluids first mix on the surface.

2. The device of claim 1 wherein the first and second containers are each a syringe.

3. The device of claim 2 wherein the first syringe and the second syringe are substantially of the same volume.

4. The device of claim 1 wherein the first and second containers are pipettes.

5. The device of claim 4 wherein each of the first and second fluid pressurizer is a plunger.

6. The device of claim 1 wherein the means for separately atomizing the first and second biochemically reactive fluids into an aerosol is a spray unit capable of delivering the first and second biochemically reactive fluids without clogging.

7. A medical device for laparoscopically delivering volumetric quantities of a first and a second biochemically reactive fluid comprising:

a first container having a first fluid opening, the first container being adapted to contain the first biochemically reactive fluid;

a second container having a second fluid opening adjacent the first fluid opening, the second container being adapted to contain the second biochemically reactive fluid;

a spray unit in fluid communication with the first container and the second container, the spray unit being capable of separately atomizing the first and second biochemically reactive fluids into an aerosol with an energy selected from the group consisting of liquid energy, mechanical energy, vibration energy, and electric energy;

a fluid pressurizer for pressurizing the first and the second biochemically reactive fluids for delivery under pressure through the spray unit onto a surface; and wherein the first and second biochemically reactive fluids first mix on the surface.

* * * * *

UNITED STATES PATENT AND TRADEMARK OFFICE

CERTIFICATE OF CORRECTION

PATENT NO. : 5,989,215

DATED : November 23, 1999

Figure 6A:
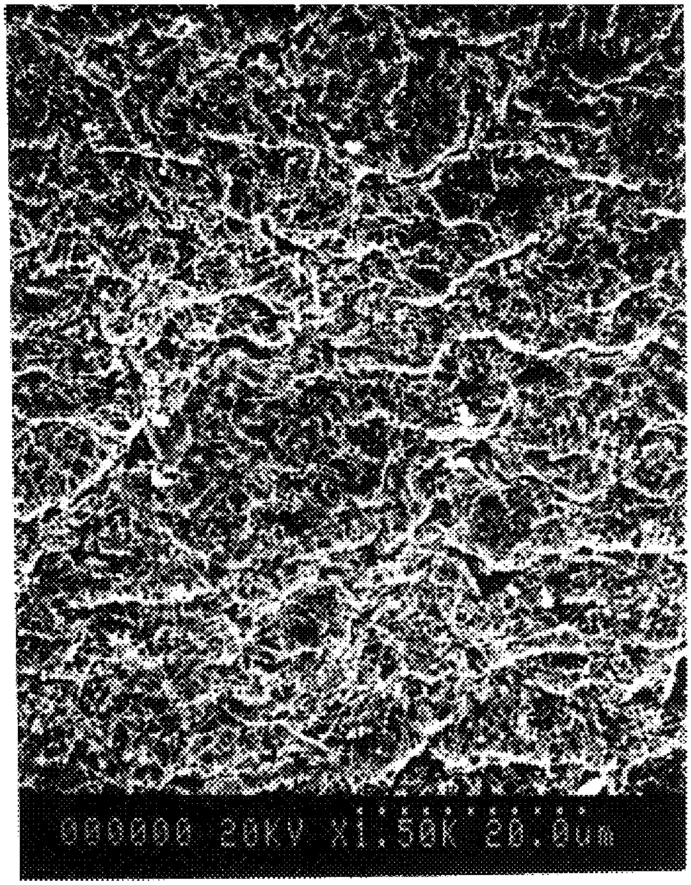
FIG. 6 is a scanning electron microscopy (SEM) of a fibrin film made of 3 IU of thrombin (mag. 1,5 K and 5.0 K). The pore size is about 3–4 μm.
Figure 6B:
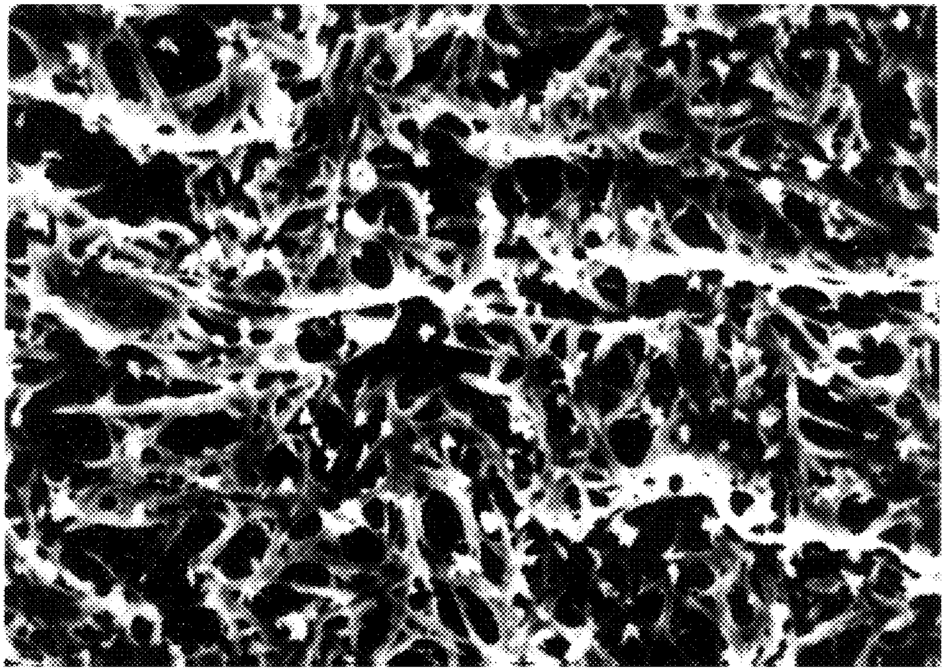
Figure 7A:
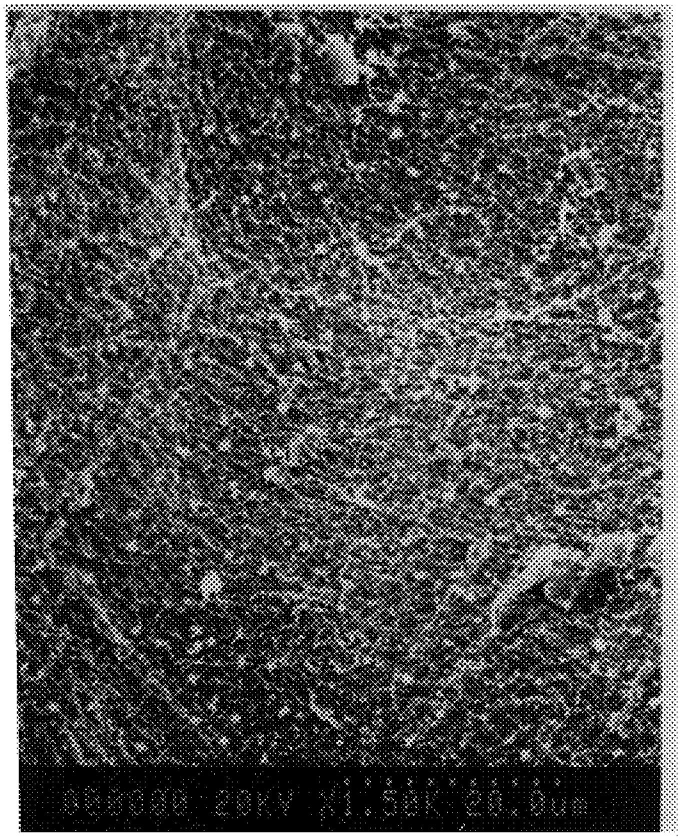
FIG. 7 is a SEM of fibrin film made with 300 IU of thrombin (x 1,5 K, x 5.0 K). The pore size is about 0.2 μm.
Figure 7B:
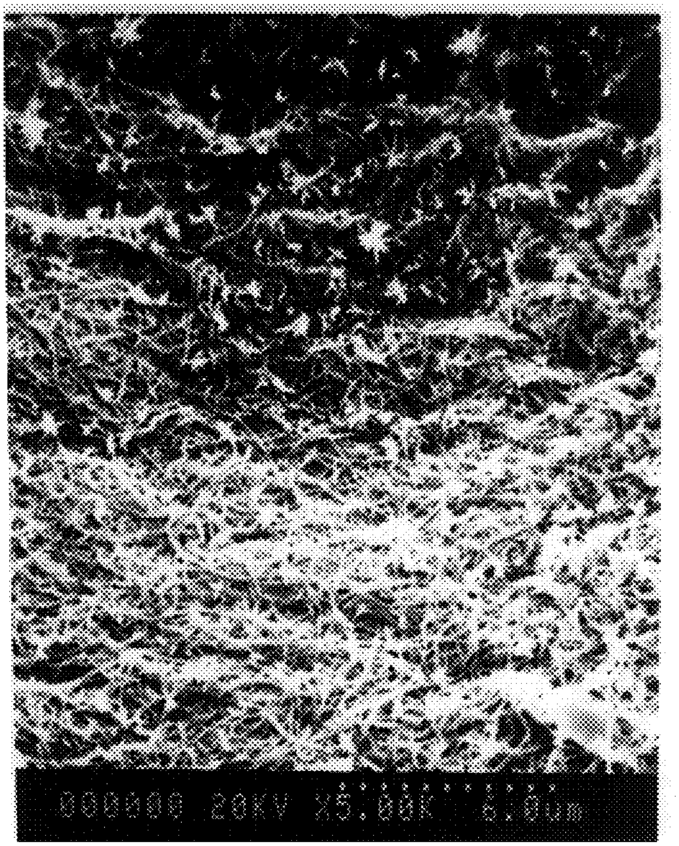
Figure 8A:
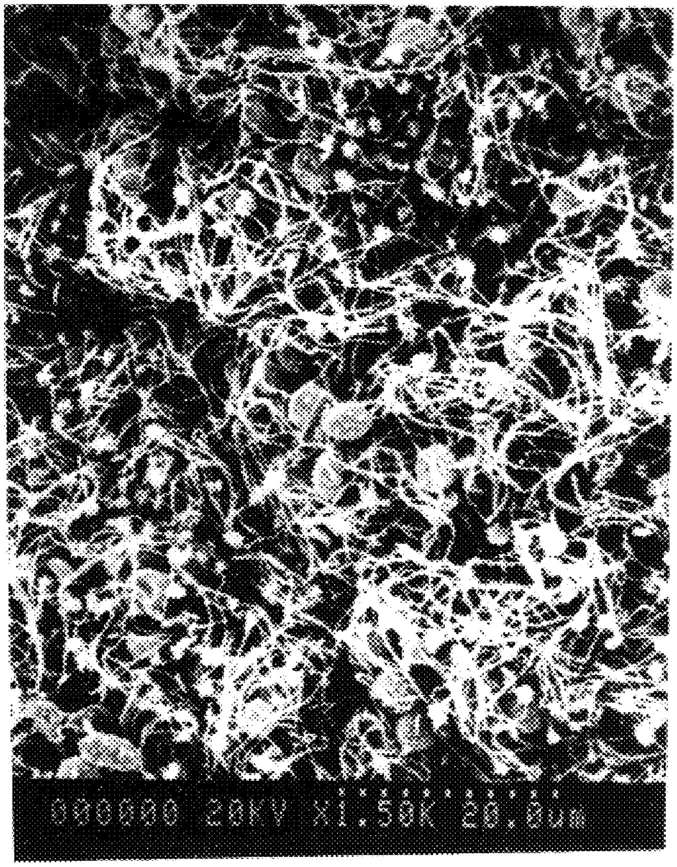
FIG. 8 is a SEM observation of a blood clot obtained by mixing 100 μm of autologous blood with 100 μm of 20 mM $CaCl_2$ (x 1,5 K, x 5.0 K)
Figure 8B:
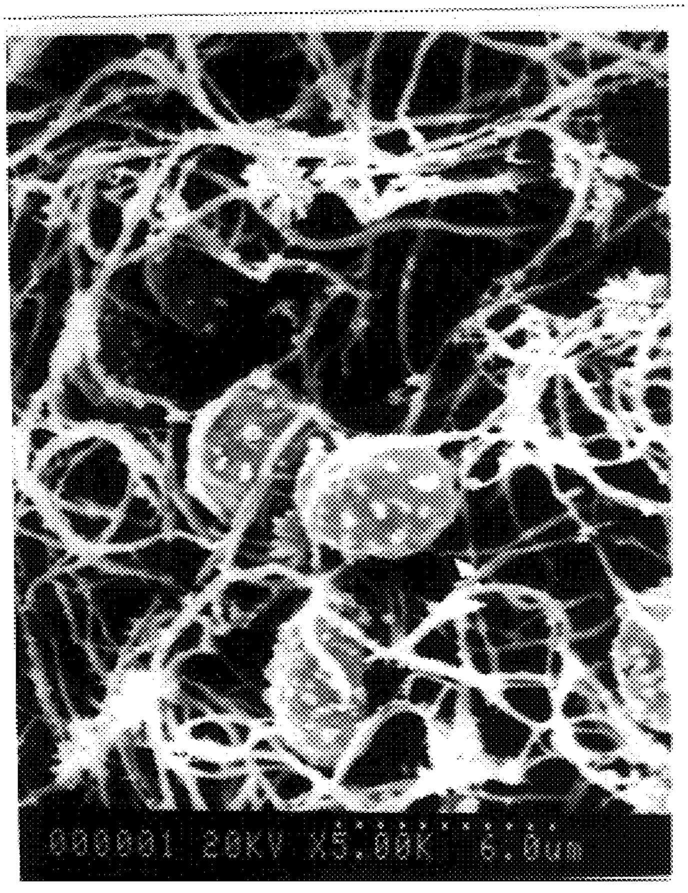
Figure 9A:
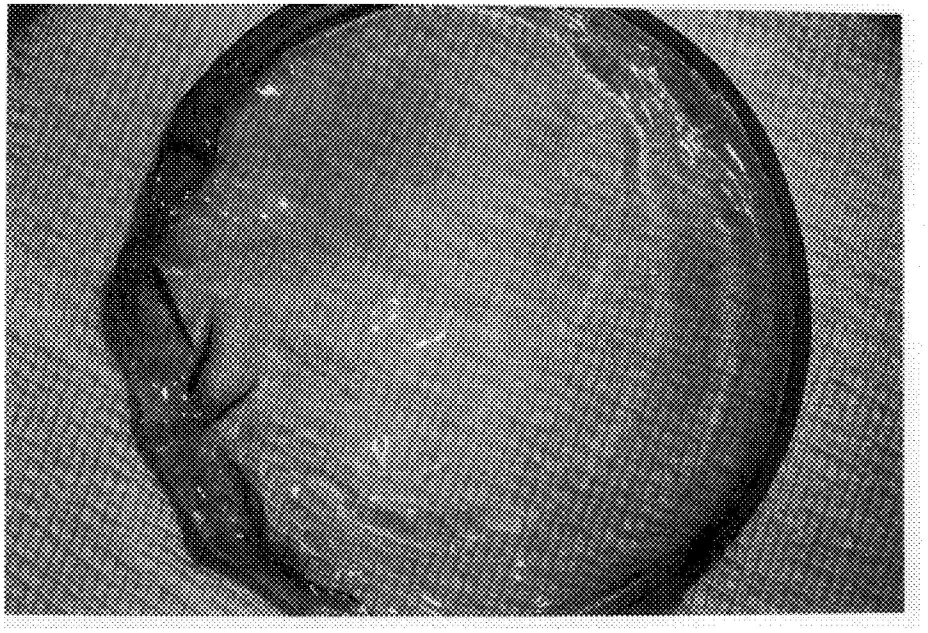
FIG. 9A is a fibrin film in accordance with Example 1, containing methylene blue as a disinfectant.
Figure 9B:
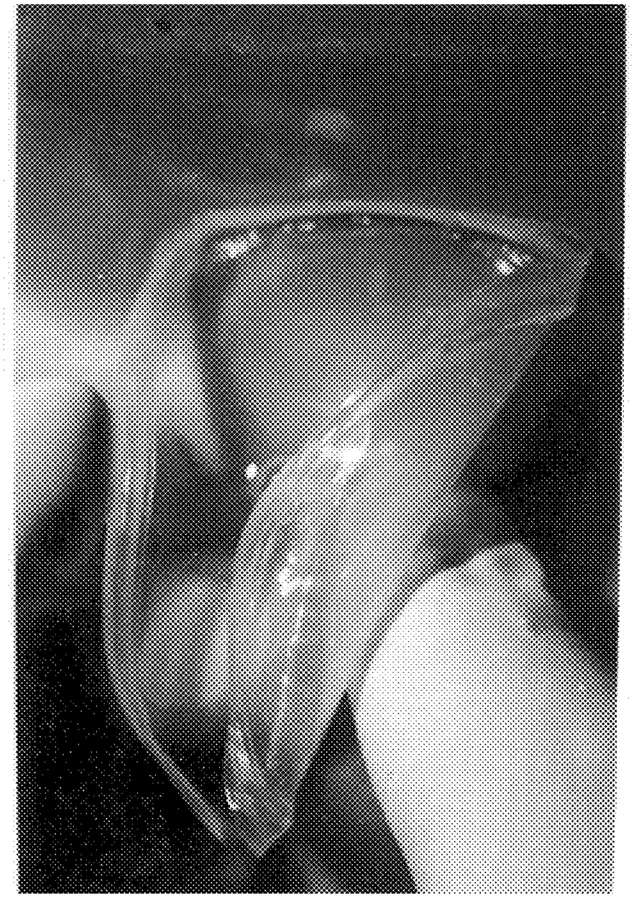
FIG. 9B is a fibrin film in accordance with Example 2.
Figure 10A:
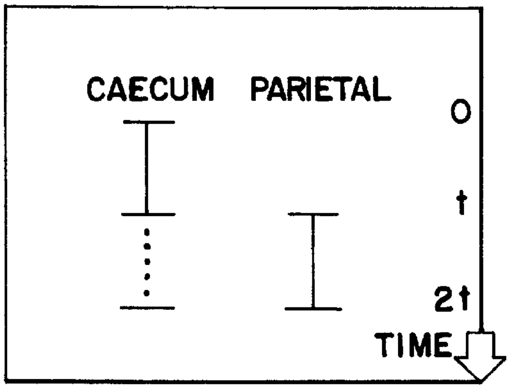
FIG. 10 is a scheme showing the different types and modes of application using fibrin glues.
Figure 10B:
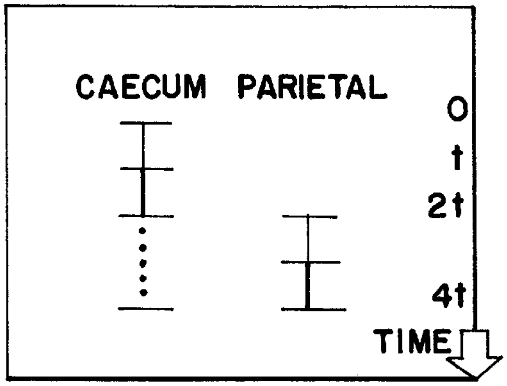
Figure 10C:
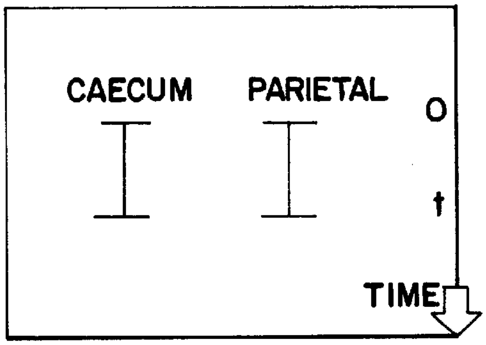
Figure 10D:
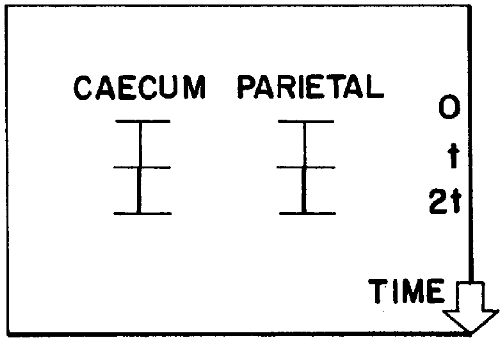
Figure 11:
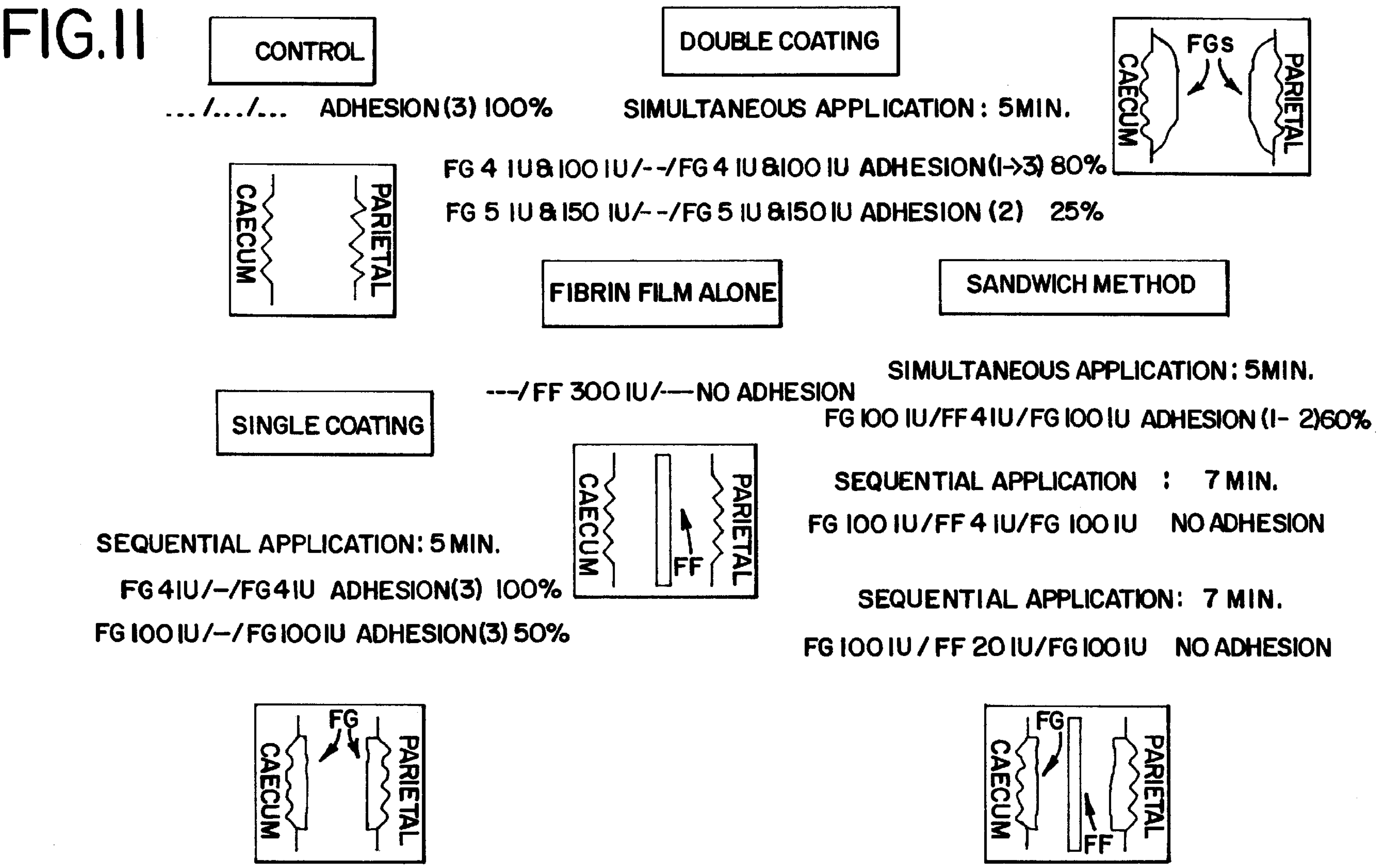
FIG. 11 is a scheme summarizing the different embodiments of the invention according to the different experimental approaches.
Figures 12A, 12B, 12C, 12D, 12E:
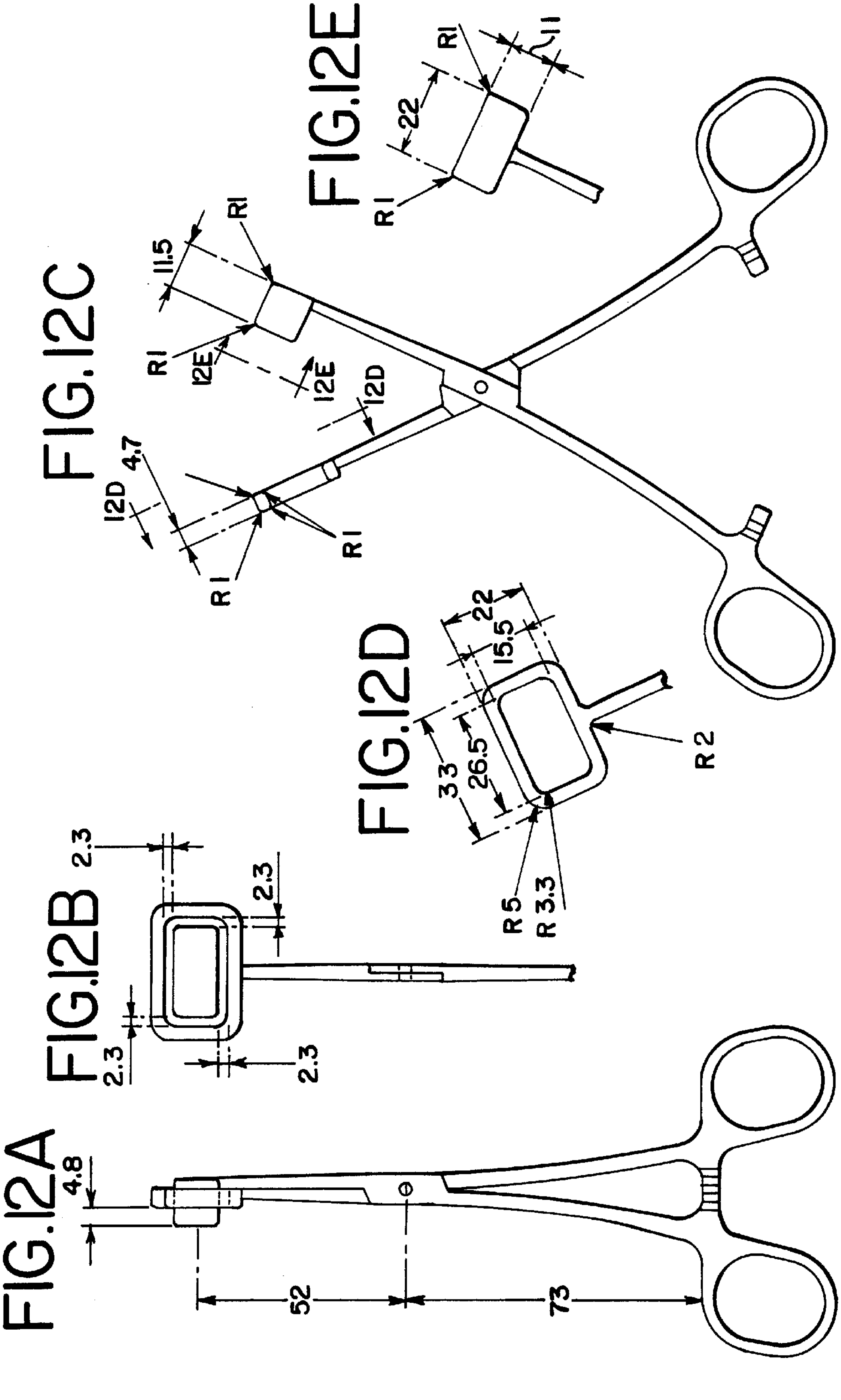
FIG. 12 is a technical drawing showing different views of the clamp having been used in the course of the animal model.

INVENTOR(S) : Yves Delmotte, Arnold Bilstad, David Amrani, Mark Kennedy and James DiOrio It is certified that error appears in the above-indentified patent and that said Letters Patent is hereby corrected as shown below:

| Column | Line | |
|---|---|---|
| 4 | 26 | Replace "Fig. 6 is a" with - - Fig. 6a and Fig. 6b are - -; Replace "microscopy" with - - microscopies - - |
| 4 | 29 | Replace "Fig. 7 is a SEM" with - - Fig. 7a and Fig. 7b are SEMs - - |
| 4 | 31 | Replace "Fig. 8 is a" with - - Fig. 8a and Fig. 8b are - - Replace "observation" with - - observations - - |
| 4 | 37 | Replace "Fig. 10 is a scheme" with - - Figs. 10a, 10b, 10c and 10d are schemes - - |
| 4 | 42 | Replace "Fig. 12 is a" with - - Figs. 12a, 12b, 12c, 12d, and 12e are - - Replace "drawing" with - - drawings - - |

Signed and Sealed this

Seventeenth Day of April, 2001

Attest:

NICHOLAS P. GODICI

*Attesting Officer*

*Acting Director of the United States Patent and Trademark Office*